United States Patent
Hasan et al.

(10) Patent No.: US 11,547,300 B2
(45) Date of Patent: Jan. 10, 2023

(54) METHODS OF TREATING AND IMAGING TUMOR MICROMETASTASES USING PHOTOACTIVE IMMUNOCONJUGATES

(71) Applicant: THE GENERAL HOSPITAL CORPORATION, Boston, MA (US)

(72) Inventors: Tayyaba Hasan, Boston, MA (US); Bryan Q. Spring, Boston, MA (US); Akilan Palanisami, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 393 days.

(21) Appl. No.: 15/114,881

(22) PCT Filed: Feb. 2, 2015

(86) PCT No.: PCT/US2015/014077
§ 371 (c)(1),
(2) Date: Jul. 28, 2016

(87) PCT Pub. No.: WO2015/117067
PCT Pub. Date: Aug. 6, 2015

(65) Prior Publication Data
US 2016/0345834 A1    Dec. 1, 2016

Related U.S. Application Data

(60) Provisional application No. 61/934,210, filed on Jan. 31, 2014.

(51) Int. Cl.
*A61B 5/00* (2006.01)
*A61K 49/00* (2006.01)
(Continued)

(52) U.S. Cl.
CPC ........ *A61B 5/0071* (2013.01); *A61B 1/00009* (2013.01); *A61B 1/00057* (2013.01);
(Continued)

(58) Field of Classification Search
CPC .............. A61B 5/0071; A61B 1/00009; A61B 1/00057; A61B 1/043; A61B 5/0084;
(Continued)

(56) References Cited

U.S. PATENT DOCUMENTS 7,809,428 B2 * 10/2010 Elmaleh ............... A61B 5/0071
600/436
8,524,239 B2 * 9/2013 Kobayashi ......... A61K 47/6869
424/178.1
(Continued)

OTHER PUBLICATIONS

Kobayashi et al., Target-cancer cell specific activatable fluorescence imaging Probes: Rational Design and in vivo Applications. Acc Chem Res (2011). 44(2) p. 83-90.*
(Continued)

*Primary Examiner* — Catherine B Kuhlman
*Assistant Examiner* — Sean A Frith
(74) *Attorney, Agent, or Firm* — Quarles & Brady LLP

(57) ABSTRACT

Methods for evaluating micrometastases in a tissue region of a subject are described. The methods include administering to the subject a detectably effective amount of a tumor-targeted photoactivatable immunoconjugate; allowing a sufficient amount of time for the tumor-targeted photoactivatable immunoconjugate to enter micrometastases in the tissue region; illuminating the tumor-targeted photoactivatable immunoconjugate; obtaining an image of the tissue region of the subject using a fluorescent imaging device, and evaluating the micrometastases in the tissue region by conducting algorithmic analysis of the image. Methods of treating micrometastases in a tissue region of a subject are also described.

16 Claims, 25 Drawing Sheets

(51) Int. Cl.
| | |
|---|---|
| *A61K 41/00* | (2020.01) |
| *G06T 7/00* | (2017.01) |
| *G01J 1/48* | (2006.01) |
| *A61B 1/00* | (2006.01) |
| *A61B 1/04* | (2006.01) |

(52) U.S. Cl.
CPC .......... *A61B 1/043* (2013.01); *A61B 5/0084* (2013.01); *A61B 5/4325* (2013.01); *A61B 5/7203* (2013.01); *A61K 41/0057* (2013.01); *A61K 49/0036* (2013.01); *A61K 49/0058* (2013.01); *G01J 1/48* (2013.01); *G06T 7/0012* (2013.01); *A61B 5/725* (2013.01); *G06T 2207/10064* (2013.01); *G06T 2207/30024* (2013.01)

(58) Field of Classification Search
CPC . A61B 5/4325; A61B 5/7203; A61B 41/0057; A61B 5/725; A61K 49/0036; A61K 49/0058; A61K 41/0057; G01J 1/48; G06T 7/0012; G06T 2207/10064; G06T 2207/30024
See application file for complete search history.

(56) References Cited

U.S. PATENT DOCUMENTS

| | | | | |
|---|---|---|---|---|
| 8,527,250 | B2* | 9/2013 | Graf | G16H 50/50 703/11 |
| 9,517,013 | B2* | 12/2016 | Kaneko | G01N 21/6456 |
| 2002/0177149 | A1* | 11/2002 | Rimm | G01N 21/6458 435/6.16 |
| 2002/0197262 | A1 | 12/2002 | Hasan et al. | |
| 2003/0086608 | A1* | 5/2003 | Frost | G01N 15/147 382/173 |
| 2007/0020272 | A1* | 1/2007 | Hasan | A61K 41/0057 530/391.1 |
| 2008/0260650 | A1* | 10/2008 | Tawakol | A61K 51/0491 424/9.37 |
| 2010/0016669 | A1* | 1/2010 | Takaoka | A61B 1/043 600/160 |
| 2011/0110567 | A1* | 5/2011 | Jiang | A61B 5/0059 382/128 |
| 2012/0253191 | A1* | 10/2012 | Zheng | A61P 43/00 514/249 |
| 2013/0230866 | A1* | 9/2013 | Miyashita | G01N 21/6428 435/7.23 |
| 2013/0287702 | A1* | 10/2013 | Brady-Kalnay | A61K 49/0058 424/9.6 |
| 2014/0005250 | A1* | 1/2014 | Byrd | G01N 33/57426 514/44 A |

OTHER PUBLICATIONS

Zhong et al., In vivo high-resolution fluorescence microendoscopy for ovarian cancer detection and treatment monitoring. British Journal of Cancer (2009) 101 p. 2015-2022.*
Ardeshirpour et al., Using In-vivo Fluorescence Imaging in Personalized Cancer Diagnostics and Therapy, an Image and Treat Paradigm. Technol Cancer Res Treat (2011). 10(6) p. 549-560.*
Mitsunaga et al., Cancer Cell-Selective In Vivo Near Infrared Photoimmunotherapy Targeting Specific Membrane Molecules. Nat Med (2012). 17(12) p. 1685-1691.*
Denis et al. Synthesis, bioanalysis and biodistribution of photosensitizer conjugates for photodynamic therapy. Bioanalysis (2013). 5(9) p. 1099-1114.*
Spiess, P., "Prostate Cancer—Diagnostic and Therapeutic Advances," Intech, 2011. p. 1-378 (Year: 2011).*
Rizvi et al., "Synergistic Enhancement of Carboplatin Efficacy with Photodynamic Therapy in a Three-dimensional Model for Micrometastatic Ovarian Cancer," Cancer Res., 2010. 70(22) p. 9319-9328 (Year: 2010).*
Hamilton, Nicholas. "Quantification and its applications in fluorescent microscopy imaging." Traffic 10.8 (2009): 951-961.
Mitsunaga, Makoto, et al. "Cancer cell-selective in vivo near infrared photoimmunotherapy targeting specific membrane molecules." Nature medicine 17.12 (2011): 1685-1691.
Zhong, W., et al. "In vivo high-resolution fluorescence microendoscopy for ovarian cancer detection and treatment monitoring." British journal of cancer 101.12 (2009): 2015-2022.
PCT International Search Report for PCT/US15/14077, dated Apr. 28, 2015, 1 page.
Savellano, M., et al., "Targeting Cells That Overexpress the Epidermal Growth Factor Receptor with Polyethylene Glycolated BPD Verteporfin Photosensitizer Immunoconjugates" photochemistry and photobiology. Apr. 2003; vol. 7, No. 4, Apr. 3, 2002 (Apr. 2003), pp. 431-439.
Spring B.Q. et al., "Selective treatment and monitoring of disseminated cancer micrometastases in vivo using dual-function, activatable immunoconjugates." Proceedings National Academy of Sciences PNAS, vol. 111, No. 10, Feb. 26, 2014, pp. E933-E942.
Spring B.Q. et al., "Microscale receiver operating characteristic analysis of micrometastasis recognition using activatable fluorescent probes indicates leukocyte imaging as a critical factor to enhance accuracy." International Society for Optical Engineering, Spie, vol. 19, No. 6, Jun. 2014, p. 66006.
European search report corresponding to European Application No. 15743124.8, dated Jan. 9, 2017, pp. 1-10.
European Examination Report for corresponding Application Serial No. 15743124.8, dated Oct. 16, 2019, pp. 1-7.
Savellano, Mark D., and Tayyaba Hasan. "Targeting Cells That Overexpress the Epidermal Growth Factor Receptor with Polyethylene Glycolated BPD Verteporfin Photosensitizer Immunoconjugates¶." Photochemistry and photobiology 77.4 (2003): 431-439.
Spring, Bryan Q., Akilan Palanisami, and Tayyaba Hasan. "Microscale receiver operating characteristic analysis of micrometastasis recognition using activatable fluorescent probes indicates leukocyte imaging as a critical factor to enhance accuracy." Journal of biomedical optics 19.6 (2014): 066006.
Spring, Bryan Q., et al. "Selective treatment and monitoring of disseminated cancer micrometastases in vivo using dual-function, activatable immunoconjugates." Proceedings of the National Academy of Sciences 111.10 (2014): E933-E942.
Ashton, Jeffrey R., Jennifer L. West and Cristian T. Badea. "In vivo small animal micro-CT using nanoparticle contrast agents." Frontiers in Pharmacology Nov. 2015, vol. 6, Article 256, pp. 1-22.
Celli, Jonathan P., Bryan Q. Spring, Imran Rizvi, Conor L. Evans, Kimberley S. Samkoe, Sarika Verma, Brian W. Pogue and Tayyaba Hasan. "Imaging and Photodynamic Therapy: Mechanisms, Monitoring, and Optimization." Chemical Reviews 2010, vol. 110, No. 5, pp. 2795-2838. 2010 American Chemical Society, published on Web Mar. 30, 2010.
Coakley, Fergus V., MD, Patricia H. Choi, MD, Christina A. Gougoutas, MD, Bhavana Pothuri, MD, Ennapadam Venkatraman, PhD, Dennis Chi, MD, Antonina Bergman, MD, PhD, Hedvig Hricak, MD, PhD. "Peritoneal Metastases: Detection with Spiral CT in Patients with Ovarian Cancer." Published online before print 10.1148/radiol.2232011081 Radiology 2002; 223:495-499.
Kinsella, Joseph M., Rebecca E. Jimenez, Priya P. Karmali, Anthony M. Rush, V. Ramana Kotamraju, Nathan C. Gianneschi, Erkki Ruoslahti, Dwayne Stupack, and Michael J. Sailor. "X-ray Computed Tomography Imaging of Breast Cancer using Targeted Peptide-Labeled Bismuth Sulfide Nanoparticles." Published in final edited form as: Angew Chem Int Ed Engl. Dec. 1, 20116; 50(51): 12308-12311.doi:10.1002/anie.201104507.
Rabin, Oded, J. Manuel Perez, Jan Grimm, Gregory Wojtkiewicz and Ralph Weissleder. "An X-ray computed tomography imaging agent based on long-circulating bismuth sulphide nanoparticles." Nature Publishing Group, nature materials, vol. 5, Feb. 2006, www.nature.com/naturematerials, pp. 118-122.
Gadducci, A., S. Cosio, P. Zola, F. Landoni,T. Maggino§ and E. Sartori. "Surveillance procedures for patients treated for epithelial ovarian cancer: a review of the literature." © 2007 IGCS and ESGO, International Journal of Gynecological Cancer 17, 21-31.

(56) References Cited

OTHER PUBLICATIONS

Coakley, F. V. et al. Peritoneal Metastases: Detection with Spiral CT in Patients with Ovarian Cancer. Radiology 223, 495499 (2002), and Gadducci, A. et al. Surveillance procedures for patients treated for epithelial ovarian cancer: a review of the literature. International Journal of Gynecological Cancer 17, 2131 (2007).

* cited by examiner

METHODS OF TREATING AND IMAGING TUMOR MICROMETASTASES USING PHOTOACTIVE IMMUNOCONJUGATES

CROSS-REFERENCE TO RELATED APPLICATIONS

This application claims priority from U.S. Provisional Application Ser. No. 61/934,210 filed Jan. 31, 2014, the entire contents of which are incorporated herein by reference.

GOVERNMENT FUNDING

This invention was made with government support under Grant Nos. RO1-AR40352, RC1-CA146337, RO1-CA160998, and PO1-CA084203, awarded by the National Institutes of Health. The government has certain rights in the invention.

BACKGROUND

Metastatic disease remains the main cause of cancer-related death despite advances in cytoreductive surgery and chemotherapy. An ongoing dilemma is the lack of options to address residual micrometastases that escape standard treatments and detection by current imaging technologies. Pantel et al., Nat Rev Clin Oncol 6:339-351 (2009). In addition to spread via hematogenous and lymphatic routes, diffuse micrometastatic spread throughout anatomical cavities is also problematic, including peritoneal dissemination resulting from cancers of the colon, pancreas, and ovary. These obstacles are pronounced in the treatment of epithelial ovarian cancer (EOC), a prime example of a frequently recurrent disease characterized by residual micrometastases. Due to the lack of screening methods or distinct symptoms during early progression, the vast majority of EOC cases are diagnosed once the disease has metastasized and formed numerous nodules studding the peritoneal cavity. Lengyel E., The American Journal of Pathology 177:1053-1064 (2010). Although a significant fraction of patients (~35%) appear to achieve a complete response after cytoreductive surgery and follow-up chemotherapy, a small number of cells with intrinsic or acquired resistance are responsible for recurrence and poor survival. These residual micrometastases are clinically occult until gross recurrence, which is often refractory to standard treatments. Laparotomy, an invasive surgical reassessment, frequently fails to detect residual disease (Selman A E, Copeland L J, Curr Oncol Rep 1:71-76 (1999)) while non-invasive clinical imaging modalities also have poor sensitivity for subcentimeter tumors. Soussan et al., Eur Radiol 22:1479-1487 (2012).

Targeted agents carrying 'always on', unquenched chromophores have emerged for targeted therapy and imaging at the macroscale. In a promising clinical study, intraoperative visualization of EOC nodules labeled with a targeted, 'always on' fluorescent probe facilitated the identification of more tumor deposits by surgeons compared to conventional bright-field illumination. van Dam et al., Nat Med 17:1315-1319 (2011). This development may ultimately translate to fluorescence-guided resection for more radical cytoreductive surgery, leaving less disease behind. Nguyen et al., Proc Natl Acad Sci USA 107:4317-4322 (2010). Photoimmunotherapy (PIT) using 'always on' immunoconjugates is a targeted form of photodynamic therapy—first reported in the seminal works of Levy and colleagues (Mew et al., J Immunol 130:1473-1477 (1983))—that has been shown to hold promise by us (Molpus et al., Gynecologic Oncology 76:397-404 (2000); Rizvi et al. Isr J Chem 52:776-787 (2012)) and by others. Van Dongen et al., Advanced Drug Delivery Reviews 56:31-52 (2004). Because photodynamic agents are mechanistically distinct from traditional treatment modalities, are effective against radio- and chemoresistant cells, and can also re-sensitize resistant cells to chemotherapy, the development of PIT is of importance for overcoming drug-resistance. In fact, photodynamic therapy has been used in the treatment of disseminated peritoneal disease with some success intraoperatively and endoscopically in the lung, bladder and esophagus. Hahn S M et al., Clin Cancer Res 12:2517-2525 (2006).

Integrating the concepts of targeted therapy and imaging, a recent proof-of-concept study performed dual epidermal growth factor receptor (EGFR)-targeted PIT and imaging of localized, macroscopic tumors using 'always on' immunoconjugates. Mitsunaga M et al., Nat Med 17:1685-1691 (2011). This study used a mouse model derived from subcutaneous implantation of A431 squamous-cell carcinoma cells that express abnormally high levels of EGFR. A limitation of PIT is persistent phototoxicity and background signal in non-target tissues due to unbound and circulating 'always on' immunoconjugates, which compromise treatment- and imaging-selectivity at the microscale. It therefore remains uncertain if PIT is safe and effective for treatment of micrometastases—the ultimate test of treatment selectivity. It is also unknown if 'always on' immunoconjugates have sufficient tumor selectivity for treatment and imaging of tumors that express more realistic levels of the target molecule.

SUMMARY OF THE INVENTION

To address the challenges associated with treating and detecting occult, residual and drug-resistant micrometastases prior to gross recurrence, it is necessary to develop (i) targeted treatments with high tumor-selectivity and distinct mechanisms of cell death to overcome dose-limiting toxicities and chemoresistance; and, (ii) high-resolution approaches with sufficient contrast to monitor microscopic disease. Here the inventors address both of these needs by developing an activatable construct targeted to markers overexpressed by cancer cells with dual functionality for both therapy and imaging, and integrate this into a quantitative fluorescence microendoscopy platform for longitudinal monitoring of micrometastases. This approach realizes treatment selectivity and imaging fidelity at the microscale.

Given these limitations, the inventors sought to develop a more selective type of PIT-termed tumor-targeted, activatable PIT (taPIT)—and tumor imaging based on dual-function immunoconjugates that enable activatable, near infrared (NIR)-mediated PIT as well as activatable fluorescence imaging (FIG. 4A-F). This approach—building on the concept of lysosome-activated imaging probes suggested by Achilefu, Urano and Kobayashi—not only achieves greater treatment selectivity than 'always on' PIT but also enables resolution of microscopic tumor deposits. Urano et al., Nat Med 15:104-109 (2008); Lee et al., Bioconjug Chem 22:777-784 (2011).

Here the inventors demonstrate these concepts of dual-function, tumor-targeted activatable immunoconjugates for selective treatment and quantitative, longitudinal imaging of micrometastases in vivo using a clinically-motivated model of advanced-stage ovarian carcinomatosis. Molpus et al., Int J Cancer 68:588-595 (1996). In this model, peritoneal micrometastases are derived from human EOC cells (OVCAR5) that possess intrinsic resistance to chemotherapy. Using activatable immunoconjugates, a custom-built microendoscope (Zhong et al., Br J Cancer 101:2015-2022 (2009)) and a newly developed image analysis workflow (FIGS. 10 and 11), the inventors present minimally invasive, quantitative and repeated measurements of micrometastases during therapy. Using fluorescence microendoscopy to characterize immunoconjugate pharmacokinetics and to monitor micrometastatic burden reduction in vivo, the inventors demonstrate tumor-selective immunoconjugate activation and taPIT efficacy. This targeted activation significantly reduces nonspecific phototoxicity and fluorescence to provide therapeutic response monitoring of microscopic tumor nodules in a complex model of disseminated disease.

Cet-BPD (no light, 1-2 treatment cycles), n=15 mice; taPIT (50 J·cm$^{-1}$, 2 cycles), n=8 mice; taPIT and chemotherapy (50-100 J·cm$^{-1}$, 1-2 cycles), n=22 mice. Asterisks denote statistically significant differences compared to untreated EOC mice, or among the indicated treatment groups (*P<0.05 *P<0.001, Kruskal-Wallis one-way ANOVA test). (C) The integrated tumor signal from in vivo fluorescence microendoscopy videos of 1 cm$^2$ biopsies compared with qRT-PCR analysis performed on matched specimens. The shaded regions indicate biopsies found to either be tumor negative (lower left box) or positive (upper right box) by both in vivo imaging and qRT-PCR. (D) Longitudinal fluorescence microendoscopy during Cet-BPD (no light) and taPIT treatment regimens. Scale bars are 100 µm. (E) Quantification of exemplary, individual mouse tumor fluorescence signals during the treatment time course. Solid lines indicate significant changes (P<0.05, two-tailed unpaired t-test). (F) Fluorescence microendoscopy-based normalization of the post—by the pre-treatment tumor burden corrects inter-patient variability to reveal enhanced taPIT efficacy over Cet-BPD without photoactivation. In (B) and (F), the mean±s.e.m. is overlaid on the scatter plots of individual results: Cet-BPD (no light, 2 cycles), n=8 mice; taPIT (50 J·cm$^{-1}$, 2 cycles), n=8 mice (*P<0.001, Mann-Whitney U test).

FIG. 9 (A and B) provides graphs and images showing histopathologic validation of micrometastasis recognition by in vivo fluorescence microendoscopy. (A) Comparison of tumor signal by in vivo fluorescence microendoscopy to histopathologic grading of co-registered punch biopsies. The mean±s.e.m. is overlaid on scatter plots: no tumor, n=16 mice; tumor, n=11 mice (***P<0.001, Mann-Whitney U test). (B) Exemplary co-registered en face fluorescence microendoscopy images and vertically sectioned, H&E-stained biopsies for the data points labeled i-iii in (A). Scale bars are 100 µm for fluorescence microendoscopy and H&E insets, and 1 mm for H&E image mosaics.

Figure 10A:
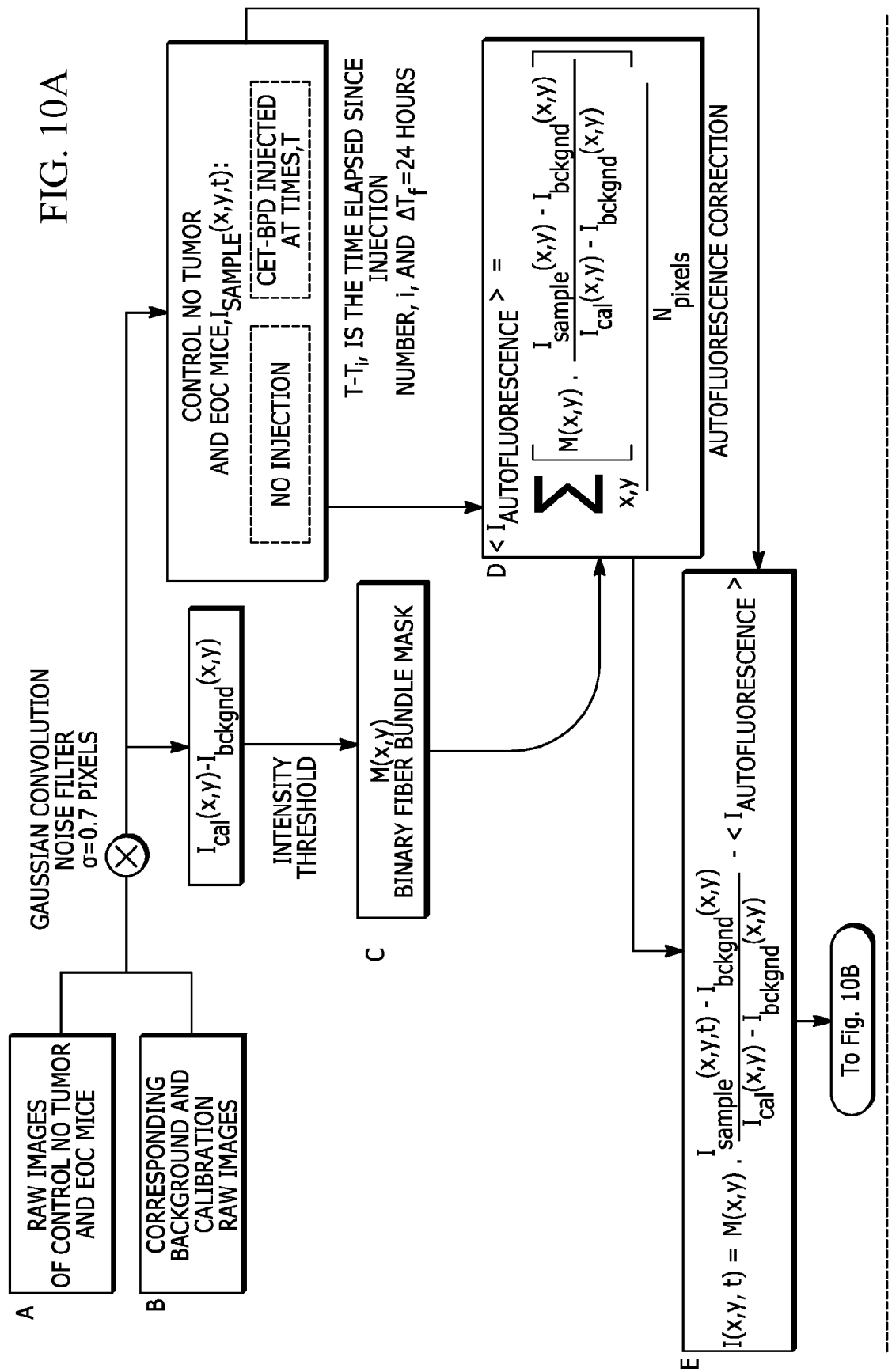
Figure 10B:
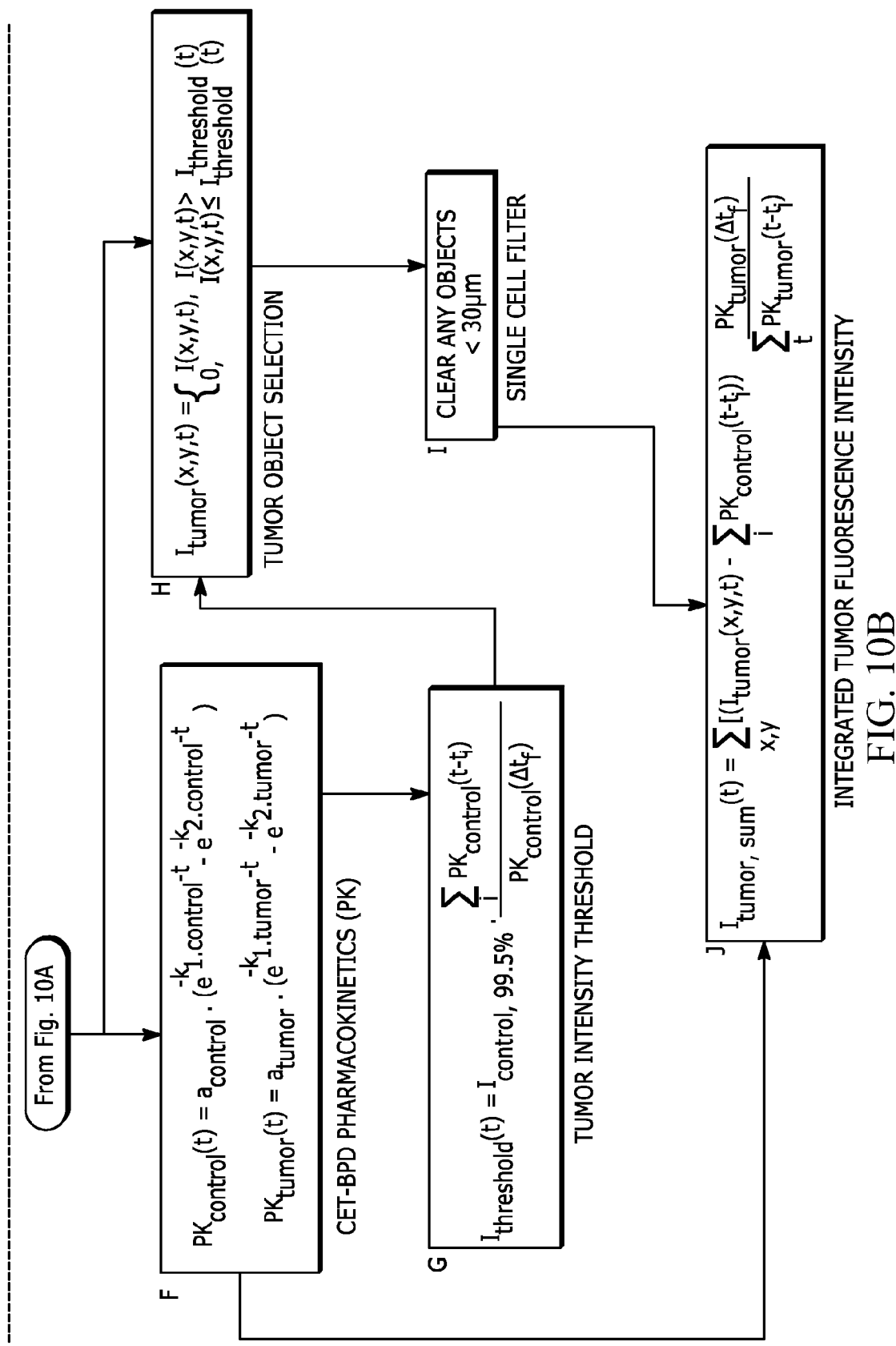

FIG. 10 provides a scheme showing the process for longitudinal micrometastatic burden quantification by in vivo fluorescence microendoscopy using an image analysis workflow that integrates multiple experiments to inform batch processing of the data.

FIG. 11 (A-C) provides quantitative intensity thresholds for tumor recognition, ROC analysis and colocalization analysis. The intensity thresholds reject >95% of pixels containing solely nonspecific background fluorescence (solid vertical lines). Frequency counts represent binning of individual pixels (n≥3 mice and numerous fields per mouse for each condition). (A) Left: exemplary intensity threshold for rejecting 99.5% of nonspecific Cet-BPD signal following a single injection. Right: validation of pharmacokinetics-informed intensity thresholds for multiple Cet-BPD injections. The pharmacokinetics-informed threshold rejects 96.2% of the background fluorescence from normal tissue in control no tumor mice that received Cet-BPD injections at 24 and 192 hours, and chemotherapy at 144 hours, prior to microendoscopy at 216 hours (i.e., 24 hours after the final Cet-BPD injection). Mean autofluorescence was subtracted prior to computing the histograms. (B, C) Intensity thresholds for rejecting 99.5% of autofluorescence (Cet-BPD, CD45 and CD31) or no tumor control (nonspecific) fluorescence (CK8). Thresholds were determined for both the ROC (B) and 3D colocalization analyses (C).

DETAILED DESCRIPTION OF THE INVENTION

The invention provides methods for imaging, treating, and quantifying cancer micrometastases. The main requirements are a molecular imaging contrast agent, a high-resolution molecular imaging instrument and post-processing software. The molecular imaging contrast agent must have high selectivity for cancer cells to provide sufficient contrast from normal background tissue to identify small deposits of cancer cells. The molecular imaging modality must have sufficient contrast to resolve microscopic objects. Finally, the image-processing software follows a workflow that is informed by measurements of background signals in normal and tumor tissues and pharmacokinetics of the molecular imaging immunoconjugate in normal and tumor tissues in order to accurately recognize (or detect) and quantify cancer micrometastases.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Image" or "imaging" refers to a procedure that produces a picture of an area of the body, for example, organs, bones, tissues, or blood.

"Pharmaceutically acceptable" as used herein means that the compound or composition is suitable for administration to a subject for the methods described herein, without unduly deleterious side effects.

As used herein, the terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

As used herein, "a detectably effective amount" of the imaging agent of the invention is defined as an amount sufficient to yield an acceptable image using equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, and the dosimetry. Detectably effective amounts of the imaging agent of the invention can also vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

The terms "comprising" and variations thereof do not have a limiting meaning where these terms appear in the description and claims.

The term "subject" for purposes of treatment includes any human or animal subject who has a disorder characterized by unwanted, rapid cell proliferation. Such disorders include, but are not limited to cancers and precancers. For methods of analysis the subject is any human or animal subject, and preferably is a human subject who has or is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

Methods for Treating Micrometastases Using Photoactivatable Immunoconjugates

In one aspect, the present invention provides a method for treating micrometastases in a tissue region of a subject. The method of treatment involves both destruction of cancer cells, and use of imaging to evaluate the effectiveness of therapy. The method includes the steps of: (a) administering to the subject a therapeutically effective amount of a tumor-targeted photoactivatable immunoconjugate; (b) allowing a sufficient amount of time for the tumor-targeted photoactivatable immunoconjugate to enter micrometastases in the tissue region; (c) photoactivating the tumor-targeted photoactivatable immunoconjugate to treat the micrometastases; (d) obtaining an image of the tissue region of the subject using a fluorescent imaging device; and (e) providing additional treatment if imaging of the tissue region indicates that a significant number of micrometastases remain in the tissue region. In some embodiments, the image of the tissue region is algorithmically analyzed before determining whether or not additional treatment is needed.

Methods of treating micrometastases include the step of photoactivating the tumor-targeted photoactivatable immunoconjugate to treat the micrometastases. The photoactivatable immunoconjugates are photoactivated by illuminating them with light having an appropriate strength and wavelength. Photoactivating of the immunoconjugates results in both a cytotoxic effect and a fluorescent effect. The cytotoxic effect involves singlet oxygen generation, which is a highly toxic compound with a short lifespan, resulting in cytotoxic damage close to the site of photoactivation. In the case of self-quenching photoactivatable compounds, this can occur only after the immunoconjugate has been taken up by cells in the micrometastases, which eliminates the quenching effect due to degradation of the antibody. The fluorescent effect involves transfer of one electron to a higher energy orbital which is unstable and is emitted as fluorescence. Photoactivation generally results in both a cytotoxic effect and a fluorescent effect; however, the nature of the light administered can encourage a higher level of one or the other. For example, higher energy light tends to increase the amount of cytotoxic effect upon photoactivation, and therefore it is beneficial to administer focused light such as that generated by a light emitting diode or laser to achieve a therapeutic effect. On the other hand, where the interest is primarily in imaging, less light is needed, and therefore it may be beneficial to administer the light using a diffusing type optical fiber for imaging applications.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, ovarian, and prostate cancer. A tumor is the physical manifestation of cancer within a subject.

Methods of the invention are also particularly suitable for use in primary treatment of intraperitoneal cancers, such as ovarian and colorectal cancers and cancer of the bladder. Other potential uses include those where combination therapies could be combined with surgical debulking, such as pleural mesothelioma or advanced stage ovarian cancer. Currently, advanced ovarian cancer is treated by staging/debulking surgery, followed by chemotherapy, which is usually a combination of Taxol and platinum-based regimen. Rather than chemotherapy, combination therapy could instead be administered. For example, an administration scheme is envisioned whereby a photoactivatable immunoconjugate composition is administered either before or after maximal debulking and subsequently light activated following the surgical procedure in order to eliminate residual cancer cells. In addition, administration of a tumor-targeted photoactivatable immunoconjugate, followed by maximal debulking, administration of a tumoricidal antibody, and subsequent light activation is also envisioned.

A micrometastases is a small number of cancer cells that have spread from the primary tumor to other parts of the body. Micrometastases are tumors having a size of less than 1 mm. However, in some embodiments the micrometastases are smaller. For example, the micrometastases can have a size of less than 0.1 mm, less than 50 µm, or a size of about 30 µm in some embodiments. Micrometastases are too small in size to be detected by conventional diagnostic or screening means.

A tissue region is an area of tissue in the subject which is being treated and/or analyzed. Generally, the tissue region is within the tissue where cancer has been identified, or tissues where it is suspected that cancer may have spread through metastasis. The tissue region can be an organ of a subject such as the heart, lungs, or blood vessels. In other embodiments, the tissue region can be diseased tissue, or tissue that is suspected of being diseased, such as a tumor or tissue regions connected with the tumor by a metastatic route or a tissue having similar characteristics to the primary tumor tissue. Examples of metastatic routes include the transcoelomic route (penetration of the surface of the peritoneal, pleural, pericardial, or subarachnoid space), lymphatic route (transport of tumor cells to lymph nodes and from there to other parts of the body), and the hematogenous route (used by sarcomas and carcinomas). The tissue region can vary widely in size, and can for example range from a size of about 1 cm$^3$ to about 500 cm$^3$.

The method of treatment includes the step of providing additional treatment if imaging of the tissue region indicates that a significant number of micrometastases remain in the tissue region. Details regarding imaging methods are described in greater detail in the discussion of imaging methods, but these methods describe equally to the treatment method which involves the step of obtaining an image of the tissue region of the subject using a fluorescent imaging device.

The step of providing additional treatment can involve administering additional tumor-targeted photoactivatable immunoconjugate to the subject. However, in other embodiments, additional treatment can include alternate forms of cancer treatment. Examples of alternate forms of cancer treatment include cryoablation, thermal ablation, radiotherapy, chemotherapy, radiofrequency ablation, electroporation, alcohol ablation, high intensity focused ultrasound, or treatment using a tumor-tarted photoactivatable immunoconjugate directed to a different epitope present on the cancer cells.

In some embodiments, the step providing additional treatment includes administering a therapeutically effective amount of an anticancer agent to the subject. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin.

Tumor-Targeted Photoactivatable Immunoconjugates

The method includes the step of administering to the subject a therapeutically effective amount of a tumor-targeted photoactivatable immunoconjugate. Tumor-targeted photoactivatable immunoconjugates are made up of a tumor-targeted antibody that is linked (i.e., conjugated) to a photoactivatable compound. Preferably, the tumor-targeted photoactivatable immunoconjugate is a tumor-targeted antibody that is linked to a plurality of photoactivatable compounds that are quenched as a result of antibody conjugation. For example, in some embodiments, 5 to 10 photoactivatable compounds may be included on each antibody, while in other embodiments, from 6 to 8 photoactivatable compounds are included on each antibody. The amount of photoactivatable compound linked to the antibody can be controlled through the amount of photoactivatable compound included in the reaction mixture, and the time allowed for linking of the photoactivatable compound to the antibody.

In some embodiments, the density of the photoactivatable compound on the antibody is sufficient to quench photoactivation while the composition is freely circulating throughout the bloodstream of a subject. In this regard, "sufficient to quench photoactivation" means that the photoactivatable compounds are packed densely enough on the antibody to ensure that dequenching cannot occur until tumor-targeted photoactivatable immunoconjugates are intracellularly localized. Intracellular localization of the immunoconjugates occurs through various routes, including receptor-mediated endocytosis. The high-density photoactivatable immunoconjugates are dequenched upon intracellular localization into target tumor cells. Intracellular dequenching of the photoactivatable immunoconjugates is mediated through hydrolytic and/or enzymatic processes (e.g. lysosomal degradation) and results in enhanced photoactivation upon administration of light. High-density photoactivatable immunoconjugates are less susceptible to photodynamic activation outside of target tumor cells, and thereby produce less collateral damage by way of background photoactivation in normal tissues.

A variety of methods are known to those skilled in the art for linking photoactivatable immunoconjugates to antibodies. For example, activated photoactivatable compound-NHS esters can be prepared and then reacted with the antibody. See, for example, U.S. Pat. No. 7,498,029, the disclosure of which is incorporated herein by reference. Activated photoactivatable compound-NHS esters, preferably N-hydroxysuccinimide active ester derivatives, can be synthesized by various methods. For example, the NHS active ester of BPD can be prepared in DMSO by mixing approximately 6 volumes of about 5 mg/ml BPD in its free mono-acid form (about 6.96 mM) with approximately 5 volumes of freshly prepared about 5 mg/ml NHS (about 43.4 mM) and approximately 5 volumes of freshly prepared about 5 mg/ml EDC (about 26.1 mM). Prior to conjugation, crude photoactivatable compound-NHS product can be purified by various methods. Specifically, the crude BPD-NHS active ester can be purified by silica gel chromatography with ethyl acetate as the elutant and methylene chloride as the loading solvent. Following evaporation of ethyl acetate from the recovered product, the purified BPD-NHS can then be reconstituted in DMSO for use in conjugation reactions. Preferably, activated photoactivatable compound-NHS esters are purified prior to their use in conjugations. Using purified photoactivatable compound-NHS preparations in the conjugation reactions advantageously permits higher photoactivatable compound:antibody molar loading ratios without sacrificing immunoconjugate purity and/or the integrity of the antibody's antigen binding activity.

Following conjugation of the antibody to a solubility agent, the purified, activated photoactivatable compound-NHS ester is introduced into the conjugation reaction mixture. Use of an approximately 50% DMSO/50% aqueous two-solvent system is advantageous in that it diminishes the tendency of the photoactivatable compound to aggregate and bind noncovalently to the photoactivatable immunoconjugate. During mixing of the various reactants, care should be taken to avoid exposing the antibody to greater than approximately 50% DMSO content, in order to prevent denaturation and/or precipitation of the protein. Use of an approximately 50% DMSO/50% aqueous two-solvent system allows efficient generation of high purity photoactivatable immunoconjugates with BPD:antibody molar loading ratios ranging from approximately 2 up to about 11. The yield of the photoactivatable compound conjugation reaction is approximately 75% for the preparation of photoactivatable immunoconjugates with BPD:antibody molar loading ratios of about 2. The photoactivatable compound conjugation reaction yield drops below approximately 45% for the preparation of photoactivatable immunoconjugates with BPD:molar loading ratios greater than about 10. Nevertheless, the observed reaction yields for conjugations that are carried out in the approximately 50% DMSO/50% aqueous two solvent system are substantially higher by comparison to the observed reaction yields for conjugations that are carried out in predominantly aqueous solutions.

The antibody component of the photoactivatable immunoconjugate can bind with specificity to an epitope present on the surface of a tumor cell. "Binding with specificity" means that noncancer cells are either not specifically bound by the antibody or are only poorly recognized by the antibody. The antibodies of the invention comprise whole native antibodies, bispecific antibodies; chimeric antibodies; Fab, Fab', single chain V region fragments (scFv) and fusion polypeptides. Preferably, the antibodies of the invention are monoclonal.

The term "antibody" as used in this invention includes intact immunoglobulin molecules as well as fragments thereof, such as Fab and Fab', which are capable of binding the epitopic determinant. Fab fragments retain an entire light chain, as well as one-half of a heavy chain, with both chains covalently linked by the carboxy terminal disulfide bond. Fab fragments are monovalent with respect to the antigen-binding site.

A wide variety of tumor-specific antibodies are known to those skilled in the art. See Scott et al., Nature, 12, 278-287 (2012), the disclosure of which is incorporated herein by reference. For example, antibodies of the invention that bind to tumor cell epitopes include, but are not limited to, IMC-C225, EMD 72000, OvaRex Mab B43.13, 21B2 antibody, anti-human CEA, CC49, anti-ganglioside antibody G(D2) ch14.18, OC-125, F6-734, CO17-1A, ch-Fab-A7, BIWA 1, trastuzumab, rhuMAb VEGF, sc-321, AF349, BAF349, AF743, BAF743, MAB743, AB1875, Anti-Flt-4AB3127, FLT41-A, rituximab, tositumomab, Mib-1, 2C3, BR96, CAMPATH 1H, 2G7, 2A11, Alpha IR-3, ABX-EGF, MDX-447, SR1, Yb5.b8, 17F.11, anti-p75, anti-p64 IL-2R and MLS 102.

A wide variety of tumor-specific antibodies are known in the art, such as those described in U.S. Pat. Nos. 6,197,524, 6,191,255, 6,183,971, 6,162,606, 6,160,099, 6,143,873, 6,140,470, 6,139,869, 6,113,897, 6,106,833, 6,042,829, 6,042,828, 6,024,955, 6,020,153, 6,015,680, 5,990,297, 5,990,287, 5,972,628, 5,972,628, 5,959,084, 5,951,985, 5,939,532, 5,939,532, 5,939,277, 5,885,830, 5,874,255, 5,843,708, 5,837,845, 5,830,470, 5,792,616, 5,767,246, 5,747,048, 5,705,341, 5,690,935, 5,688,657, 5,688,505, 5,665,854, 5,656,444, 5,650,300, 5,643,740, 5,635,600, 5,589,573, 5,576,182, 5,552,526, 5,532,159, 5,525,337, 5,521,528, 5,519,120, 5,495,002, 5,474,755, 5,459,043, 5,427,917, 5,348,880, 5,344,919, 5,338,832, 5,298,393, 5,331,093, 5,244,801, and 5,169,774. See also The Monoclonal Antibody Index Volume 1: Cancer (3rd edition). Accordingly, tumor-specific antibodies of the invention can recognize tumors derived from a wide variety of tissue types, including, but not limited to, breast, prostate, colon, lung, pharynx, thyroid, lymphoid, lymphatic, larynx, esophagus, oral mucosa, bladder, stomach, intestine, liver, pancreas, ovary, uterus, cervix, testes, dermis, bone, blood and brain.

As used in this invention, the term "epitope" means any antigenic determinant on an antigen to which the antibody binds. Epitopic determinants usually consist of chemically active surface groupings of molecules such as amino acids or sugar side chains and usually have specific three dimensional structural characteristics, as well as specific charge characteristics. Epitopes of the invention can be present, for example, on cell surface receptors.

Epitopes to which tumor-specific antibodies bind are also well known in the art. For example, epitopes bound by the tumor-specific antibodies of the invention include, but are not limited to, those known in the art to be present on CA-125, gangliosides G(D2), G(M2) and G(D3), CD20, CD52, CD33, Ep-CAM, CEA, bombesin-like peptides, PSA, HER2/neu, epidermal growth factor receptor, erbB2, erbB3, erbB4, CD44v6, Ki-67, cancer-associated mucin, VEGF, VEGFRs (e.g., VEGFR3), estrogen receptors, Lewis-Y antigen, TGF.beta.1, IGF-1 receptor, EGFα, c-Kit receptor, transferrin receptor, IL-2R and CO17-1A.

The antibodies of this invention can be prepared in several ways. Methods of producing and isolating whole native antibodies, bispecific antibodies, chimeric antibodies, Fab, Fab', single chain V region fragments (scFv) and fusion polypeptides are known in the art. See, for example, Harlow and Lane (1988) Antibodies: A Laboratory Manual, Cold Spring Harbor Laboratory, New York (Harlow and Lane, 1988).

Antibodies are most conveniently obtained from hybridoma cells engineered to express an antibody. Methods of making hybridomas are well known in the art. The hybridoma cells can be cultured in a suitable medium, and spent medium can be used as an antibody source. Polynucleotides encoding the antibody can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Another method of obtaining antibodies is to immunize suitable host animals with an antigen and to follow standard procedures for polyclonal or monoclonal production. Monoclonal antibodies (Mabs) thus produced can be "humanized" by methods known in the art. Examples of humanized antibodies are provided, for instance, in U.S. Pat. Nos. 5,530,101 and 5,585,089.

"Humanized" antibodies are antibodies in which at least part of the sequence has been altered from its initial form to render it more like human immunoglobulins. In one another version, the heavy chain and light chain C regions are replaced with human sequence. In another version, the complementarity determining region (CDR) comprises amino acid sequences for recognition of antigen of interest, while the variable framework regions have also been converted to human sequences. See, for example, EP 0329400. In a third version, variable regions are humanized by designing consensus sequences of human and mouse variable regions, and converting residues outside the CDRs that are different between the consensus sequences. The invention encompasses humanized Mabs. The invention also encompasses hybrid antibodies, in which one pair of heavy and light chains is obtained from a first antibody, while the other pair of heavy and light chains is obtained from a different second antibody. Such hybrids may also be formed using humanized heavy and light chains.

Construction of phage display libraries for expression of antibodies, particularly the Fab or scFv portion of antibodies, is also well known in the art (Heitner et al., J Immunol Methods, 248, 17-30 (2001)). The phage display antibody libraries that express antibodies can be prepared according to the methods described in U.S. Pat. No. 5,223,409 incorporated herein by reference. Procedures of the general methodology can be adapted using the present disclosure to produce antibodies of the present invention. The method for producing a human monoclonal antibody generally involves (1) preparing separate heavy and light chain-encoding gene libraries in cloning vectors using human immunoglobulin genes as a source for the libraries, (2) combining the heavy and light chain encoding gene libraries into a single dicistronic expression vector capable of expressing and assembling a heterodimeric antibody molecule, (3) expressing the assembled heterodimeric antibody molecule on the surface of a filamentous phage particle, (4) isolating the surface-expressed phage particle using immunoaffinity techniques such as panning of phage particles against a preselected antigen, thereby isolating one or more species of phagemid containing particular heavy and light chain-encoding genes and antibody molecules that immunoreact with the preselected antigen.

The tumor-targeted photoactivatable immunoconjugate also includes a photoactivatable compound. A photoactivatable compound is a compound that produces a biological effect upon photoactivation or a biological precursor of a compound that produces a biological effect upon photoactivation. Photoactivatable compound of the invention can be any known in the art, including Photofrin™, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series, chlorins, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlor-in, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, mono-acid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid benzonaphthoporphyrazines, cationic iminium salts, tetracyclines, lutetium texaphyrin, tin-etio-purpurin, porphycenes, benzophenothiazinium and combinations thereof. For a discussion of photodynamic therapy and suitable compounds, see Agostinis et al., CA Cancer J Clin., 61(4): 250-81 (2011).

In some embodiments, the photoactivatable compound is a compound capable of self quenching upon antibody loading. Examples of self-quenching compounds include silicon phthalocyanine (Pc4), porfirmer sodium (HPD), temoporfin (Foscan, mTHPC), 2-(1-hexyloxyethyl)-2-devinyl pyropheophorbide-a (HPPH), motexafin lutetium (Lutex), and benzoporphyrin derivative.

In a preferred embodiment, the photoactivatable compound is a benzoporphyrin derivative ("BPD"), such as BPD-MA, also commercially known as BPD Verteporfin ("BPD"). U.S. Pat. No. 4,883,790 describes BPDs. BPD is a so-called second-generation compound which lacks the prolonged cutaneous phototoxicity of Photofrin™. BPD has been thoroughly characterized, (Aveline et al., Photochemistry and Photobiology, 59, 328-335 (1994)), and it has been found to be a highly potent photoactivatable compound.

As proof-of-concept, the inventors have synthesized cetuximab-based immunoconjugates stemming from the inventors' observation of synergistic tumor reduction when combining cetuximab with photodynamic therapy using verteporfin. However, the concepts of tumor-targeted photoactivatable immunoconjugates and micrometastasis imaging reported here can be applied to a variety of tumor biomarkers and to address tumor heterogeneity in biomarker expression because many other tumor-targeted antibodies and antibody fragments are available. Other mAbs for use with tumor-targeted photoactivatable immunoconjugates include panitumumab, a fully humanized mAb of the IgG2 isotype, directed against EGFR and in the clinic. Panitumumab lacks the cytotoxic component of cetuximab but shares many other mechanisms of action with cetuximab, and it has been applied for cancer therapy. Mitsunaga et al., Nat Med 17:1685-1691 ((2011). As another example, trastuzumab, also applied here, can be used to target HER2 (ErbB2) overexpressing cancer cells. In addition to the ErbB family of receptors, there exists mAbs in clinical trials for a number of other cancer cell-surface biomarkers including hepatocyte growth factor/mesenchymal-epithelial transition factor RTK, epithelial cell adhesion molecule and folate receptor alpha. MAb fragments (e.g., ranibizumab) and small peptides are also emerging and have the advantage of being considerably smaller than full mAbs (for deeper tissue penetration) but lack the cytotoxic component of IgG1 s (with other pharmacokinetic and pharmacodynamic alterations relative to full mAbs).

Methods of Imaging a Tissue Region Using Photoactivatable Immunoconjugates

In one aspect, the present invention provides a method for evaluating micrometastases in a tissue region of a subject that includes the steps of: (a) administering to the subject a detectably effective amount of a tumor-targeted photoactivatable immunoconjugate; (b) allowing a sufficient amount of time for the tumor-targeted photoactivatable immunoconjugate to enter micrometastases in the tissue region; (c) illuminating the tumor-targeted photoactivatable immunoconjugate; (d) obtaining an image of the tissue region of the subject using a fluorescent imaging device, and (e) evaluating the micrometastases in the tissue region by conducting algorithmic analysis of the image.

The present invention provides a method of obtaining an image of a tissue region of a subject, by administering to the subject a detectably effective amount of a tumor-targeted photoactivatable immunoconjugate, and generating an image of the tissue region of the subject to which the immunoconjugate has distributed and then been activated. In order to generate an image of the tissue region, it is necessary for a detectably effective amount of imaging agent to reach the tissue region of interest, but it is not necessary that the imaging agent be localized in this region alone. However, in some embodiments, the tumor-targeted photoactivatable immunoconjugates are targeted or administered locally such that they are present primarily in the tissue region of interest. Examples of images include two-dimensional cross-sectional views and three dimensional images. In some embodiments, a computer is used to carry out an algorithmic analysis the data generated by the imaging agents in order to generate a visual image.

Following administration of the tumor-targeted photoactivatable immunoconjugate, it is necessary to wait for the immunoconjugate to reach an effective tissue concentration at the tumor site before photoactivation. Duration of the waiting step varies, depending on factors such as route of administration, tumor location, and speed of immunoconjugate movement in the body. In addition, where immunoconjugates target receptors or receptor binding epitopes, the rate of immunoconjugate uptake can vary, depending on the level of receptor expression and/or receptor turnover on the tumor cells. For example, where there is a high level of receptor expression, the rate of tumor-targeted photoactivatable immunoconjugate binding and uptake is increased. The waiting period should also take into account the rate at which immunoconjugates are degraded and thereby dequenched in the target tissue. Determining a useful range of waiting step duration is within ordinary skill in the art and may be optimized by utilizing fluorescence optical imaging techniques.

Following the waiting step, the tumor-targeted photoactivatable immunoconjugate is activated by photoactivating light applied to the tumor site. This is accomplished by applying light of a suitable wavelength and intensity, for an effective length of time, specifically to the lesion site. The suitable wavelength, or range of wavelengths, will depend on the particular photoactivatable compound(s) used. Wavelength specificity for photoactivation depends on the molecular structure of the photoactivatable compound. Photoactivation occurs with sub-ablative light doses. Determination of suitable wavelength, light intensity, and duration of illumination is within ordinary skill in the art.

The light for photoactivation can be produced and delivered to the tumor site by any suitable means, such as a fluorescent imaging device. For superficial tumors or open surgical sites, suitable light sources include broadband conventional light sources, broad arrays of light emitting diodes (LED), and defocussed laser beams.

For non-superficial lesion sites, including those in intracavitary settings, the photoactivating light can be delivered by optical fiber devices. For example, the light can be delivered by optical fibers threaded through small gauge hypodermic needles. Optical fibers also can be passed through arthroscopes, endoscopes and laproscopes. In addition, light can be transmitted by percutaneous instrumentation using optical fibers or cannulated waveguides.

Photoactivation at non-superficial lesion sites also can be by transillumination. Some photoactivatable compounds can be activated by near infrared light, which penetrates more deeply into biological tissue than other wavelengths. Thus, near infrared light is advantageous for transillumination. Transillumination can be performed using a variety of devices. The devices can utilize laser or non-laser sources, i.e. lightboxes or convergent light beams.

For photoactivation, the wavelength of light is matched to the electronic absorption spectrum of the photoactivatable compound so that photons are absorbed by the photoactivatable compound and the desired photochemistry can occur. Except in special situations, where the tumors being treated are very superficial, the range of activating light is typically between approximately 600 and 900 nm. This is because endogenous molecules, in particular hemoglobin, strongly absorb light below about 600 nm and therefore capture most of the incoming photons. The net effect would be the impairment of penetration of the activating light through the tissue. The reason for the 900 nm upper limit is that energetics at this wavelength may not be sufficient to produce $^1O_2$ the activated state of oxygen. In addition, water begins to absorb at wavelengths greater than about 900 nm. In general, the amenability of lasers to fiberoptic coupling makes the task of light delivery to most anatomic sites manageable.

The effective penetration depth, $\delta_{eff}$, of a given wavelength of light is a function of the optical properties of the tissue, such as absorption and scatter. The fluence (light dose) in a tissue is related to the depth, d, as: $e^{-d/\delta_{eff}}$ Typically, the effective penetration depth is about 2 to 3 mm at 630 nm and increases to about 5 to 6 nm at longer wavelengths (e.g., 700-800 nm). These values can be altered by altering the biologic interactions and physical characteristics of the photoactivatable compound. Factors such as self-shielding and photobleaching (self-destruction of the photoactivatable compound during therapy or imaging) further complicate precise dosimetry. In general, photoactivatable compounds with longer absorbing wavelengths and higher molar absorption coefficients at these wavelengths are more effective.

Light delivery can be direct, by transillumination, or by optical fiber. Optical fibers can be connected to flexible devices such as balloons equipped with light scattering medium. Flexible devices can include, for example, laproscopes, arthroscopes and endoscopes.

Imaging methods include all methods from direct visualization without use of any device and use of devices such as various scopes, catheters and optical imaging equipment, for example computer based hardware for logarithmic analysis. The photoactivatable compounds are useful with fluorescent imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

Before or during these steps, a fluorescent imaging device can be positioned around or in the vicinity of a subject (for example, an animal or a human) to detect signals emitted from the subject. The emitted signals can be processed to construct an image, for example, by logarithmic analysis. In addition, the processed signals can be displayed as images either alone or as fused (combined) images.

A fluorescent imaging system useful in the practice of the invention typically includes three basic components: (1) an appropriate source for photoactivating the photoactivatable compound, (2) a system for separating or distinguishing emissions from the photoactivatable compound, and (3) a detection system. The detection system can be hand-held or incorporated into other useful imaging devices, such as intraoperative microscopes. Exemplary detection systems include an endoscope, microendoscope, catheter, tomographic system, hand-held imaging system, or an intraoperative microscope. Because of their minimally invasive nature, a preferred imaging device is a fluorescent microendoscope. See Khemthongcharoen et al, Adv Drug Deliv Rev.; 74: 53-74 (2014), the disclosure of which is incorporated herein by reference, for a review of microendoscopic imaging techniques for cancer diagnosis.

A particularly useful emission gathering/image forming component is an endoscope. Endoscopic devices and techniques which have been used for in vivo imaging of numerous tissues and organs. Other types of emission gathering components are catheter-based devices, including fiber optics devices. Such devices are particularly suitable for intravascular imaging.

A misconception about photoactivated therapies is that they have limited application due to the finite tissue penetration depth of light. However, miniature fiber optic light conduits make it possible to reach tumors deep within the human body (e.g., as illustrated in FIG. 1F) such that photodynamic therapy of metastases and deep tumors is practical with modern technology. This is possible because light transport is made efficient using diffusing tip fibers and scattering media (intralipid emulsion) to spread the light over large areas, such as the entire pleural and peritoneal cavities. As an example, the inventors prior preclinical studies with 'always on' photodynamic agents demonstrated photoactivated tumor destruction explicitly in hepatic, pelvic, sub-gastric, diaphragmatic, spleen and bowel sites. Molpus et al., Cancer Research 56:1075-1082 ((1996). In fact, photodynamic therapy is clinically approved for treatment of bladder, lung and esophageal cancer. Furthermore, clinical trials have demonstrated feasibility, safety and efficacy for photodynamic treatment of primary tumors in the pancreas, locally malignant glioblastoma multiforme in the brain, and disseminated, metastatic tumor deposits spread throughout the pleural (resulting from non-small-cell lung cancer) and peritoneal (resulting from ovarian cancer as well as malignancies of the gastrointestinal tract) cavities. The enhanced tumor-selectivity achieved by tumor-targeted photoactivatable immunoconjugates offers promise to push this forward by enabling safe use of intense, diffuse laser light for targeted, wide-field treatment of micrometastases embedded in vital tissues. At the moment, the drug and light doses are restricted by nonspecific toxicities when using diffuse irradiation to efficiently treat disseminated disease. The cytotoxic component of tumor-targeted photoactivatable immunoconjugates is triggered by near infrared light, which has sufficient tissue penetration to treat microscopic tumors.

The methods of the invention can be used to help a physician or surgeon to identify and characterize areas of disease, such as dysplasia and cancer, to distinguish diseased from normal tissues, such as detecting specific regions of ovarian cancer within an organ or other tissues that are difficult to detect using ordinary imaging techniques, and to further assess said tissues as candidates for particular treatment regimens, or gauge the prognosis such as staging the cancer. The methods and compositions of the invention can also be used in the detection, characterization and/or determination of the localization of a disease, including early disease, the severity of a disease or a disease-associated condition, the staging of a disease, and/or monitoring a disease. The presence, absence, nature, or level of an emitted signal can be indicative of a disease state. The methods can also be used to evaluate the effectiveness of treatment to determine if micrometastases remain after treatment.

Algorithmic Image Analysis

Figure 1:
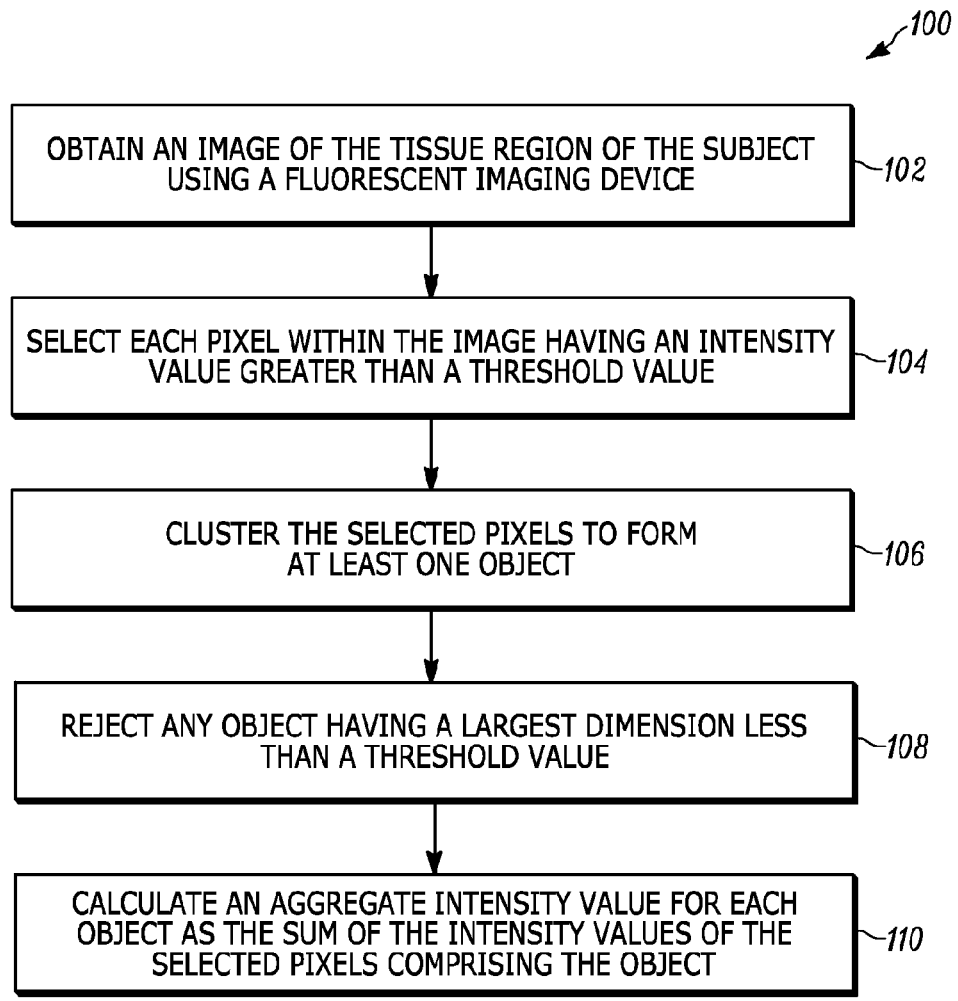
FIG. 1 is a flow diagram illustrating a method of obtaining an evaluating micrometastases in a tissue region of a subject using a fluorescent imaging device.

FIG. 1 illustrates a method 100 of evaluating micrometastases in a tissue region of a subject having been administered a therapeutically effective amount of a tumor-targeted photoactivatable immunoconjugate that has been activated. At 102, an image of the tissue region of the subject using a fluorescent imaging device, such as a microendoscope. At 104, each pixel within the image having an intensity value greater than a threshold value is selected. In one implementation, the threshold value from a plurality of intensity values taken from a control environment free of metastases and a pharmacokinetic model. At 106, the selected pixels are clustered to form at least one object. It will be appreciated that any of a number of clustering algorithms can be applied to provide the at least one identified object.

At 108, any object having a largest dimension less than a threshold value is rejected. For example, any object that is less than 30 microns can be excluded from the analysis as smaller than a human cell. At 110, an aggregate intensity value can be calculated for each object as the sum of the intensity values of the selected pixels comprising the object. This value for each object can be provided to a clinician via an appropriate output device, such as a display or printer.

Figure 2:
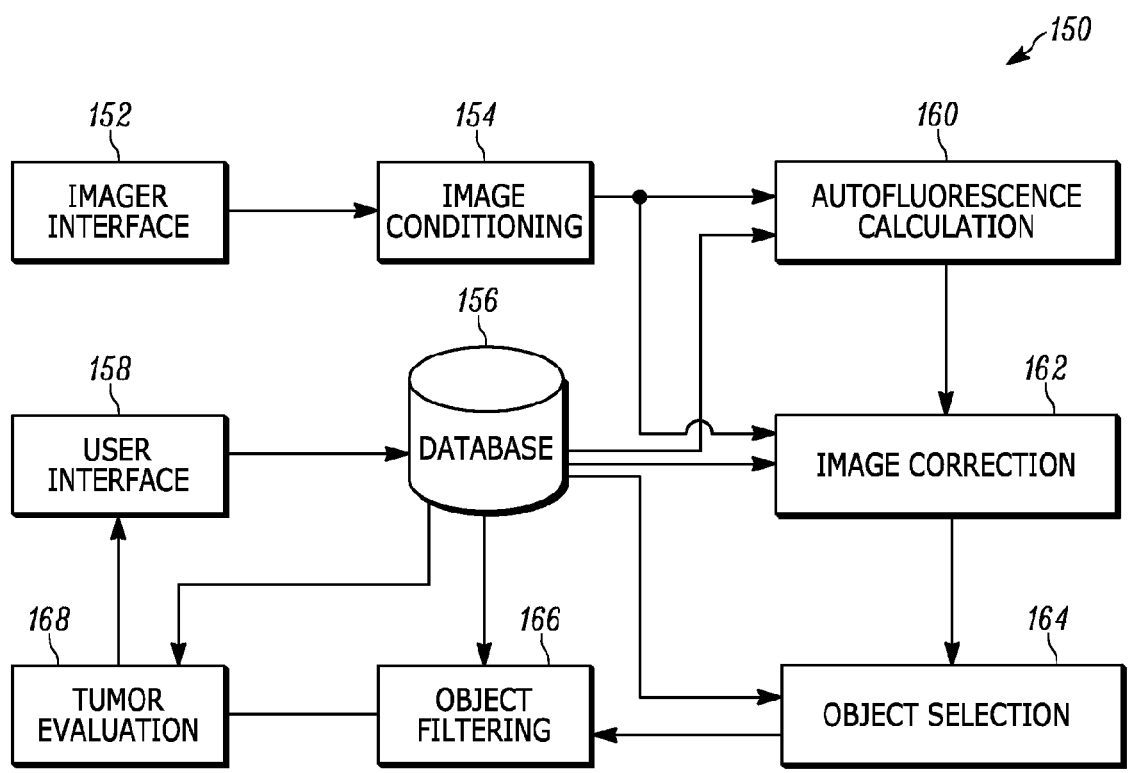
FIG. 2 illustrates a system for algorithmic analysis of an image obtained from a tissue region of a subject using tumor-targeted photoactivatable immunoconjugates.

FIG. 2 illustrates a system 150 for evaluating fluorescence images of a region of interest. It will be appreciated that the system 150 can be implemented as dedicated hardware, software operating on a general purpose processor, or a combination of dedicated hardware and software elements. An imager interface 152 is configured to receive a set of at least one fluorescence image from an associated imager. For example, the set of fluorescence images can include a set of images taken at various times after injection of an immunoconjugate as well as an image taken prior to injection. An image conditioning component 154 filters and otherwise conditions the images for analysis. In one implementation, the image conditioning component 154 applies a Gaussian convolution noise filter having a standard deviation of 0.7 pixels.

A database 156 stores information derived from previously obtained control, background, and calibration images for various types of tissues and cancers. The type of tissue and tumor relevant to a given analysis for a given set of images can be provided via a user input by a clinician or technician. The database 156 includes, for each tissue type, a set of calibration intensity values obtained from the calibration image, a set of background intensity values determined from an image of the tissue type under illumination but without the injected immunoconjugate, and one or more control images for the tissue type, representing tissue known to be free of tumors for which the immunoconjugate has been injected. In practice, there will be a control image corresponding to each of the injection times for the captured images, with the exception of any pre-injection image. The database 156 can also store recommendations for an imaging mode and contrast agent based upon the selected tissue type and cancer, as well as pharmacokinetic data for the tissue. A binary mask, representing the portion of the image likely to receive usable input, can be determined from the calibration image. A set of normalization values can be determined as the pixel-by-pixel difference between the calibration image and the background image, providing a spatially-selective effective dynamic range for the image.

An autofluorescence correction component 160 determines an autofluorescence correction for autofluorescence for the images. In one implementation, the preinjection image can be adjusted for background fluorescence with a pixel-by-pixel subtraction of the background values from the preinjection image. A pixel-by-pixel division of the adjusted preinjection image by the normalization values can then be determined and convolved with the binary mask. The resulting intensity values can then be averaged across the image to provide an autofluorescence intensity value.

An image correction component 162 corrects each of the post-injection images in the set of images. In one implementation, each of the set of images can be adjusted for background fluorescence with a pixel-by-pixel subtraction of the background values from the intensity values of the image. A pixel-by-pixel division of the adjusted image by the normalization values can then be determined and convolved with the binary mask. The calculated autofluorescence value is then subtracted from the resulting value to provide corrected intensity values for each image.

An object selection component 164 identifies a plurality of objects within the object that could represent tumors. To this end, each pixel is compared to a threshold value determined from the control images and set to zero intensity if it is equal to or below the threshold value. The remaining pixels can then be clustered to form at least one object that could represent a micrometastasis. It will be appreciated that the threshold for a given image can depend on the injection time for the image, such that multiple threshold values can be determined from control images taken at different times after injection. In one example, the threshold value can be determined by fitting the control values to a pharmacokinetic model specific to the tissue type, and multiplying one of the brightest pixels of each control image (e.g., the $99.5^{th}$ percentile pixel by intensity value) by a constant value determined from the pharmacokinetic model. For example, the constant value can represent a ratio of the sum of the intensities expected in the model given the time or times since injection(s) of immunoconjugate to a standard value, such as an expected intensity twenty-four hours after injection.

An object filtering component 166 removes any objects that are unlikely to represent a micrometastasis. In the illustrated implementation, a size-based filtering is used, in which objects smaller than a single cell are rejected as micrometastases. The specific size for the rejection filter can be determined according to a tissue type and cancer type, as well as a resolution and accuracy of the imaging device, and stored in the database 156. The image and the position of the remaining identified objects can then be provided to a tumor evaluation component 168. The tumor evaluation component 168 provides, for each object, a metric representing the size and activity of the tumor represented by the object and provides this information to a user at an appropriate output device via the user interface 158.

In one implementation, the metric provided by the tumor evaluation component 168 is an integrated tumor fluorescence value, representing an aggregate intensity from the object. In one implementation, the summed intensity values within the boundaries of each object can be provided. In another implementation, the intensity for the objects is summed both spatially and temporally across multiple images. In the illustrated implementation, the intensity values can be corrected according to the pharmacokinetic model for the tissue. To this end, each intensity value in each image can have an expected control value associated with its time since injection, and multiplied by a ratio of the standard value, such as an expected intensity twenty-four hours after injection, to the sum of the intensities expected in the model given a set of time or times since injection(s) of immunoconjugate. The resulting intensity values are summed across all images for a given object and presented as a single metric to a clinician.

Figure 3:
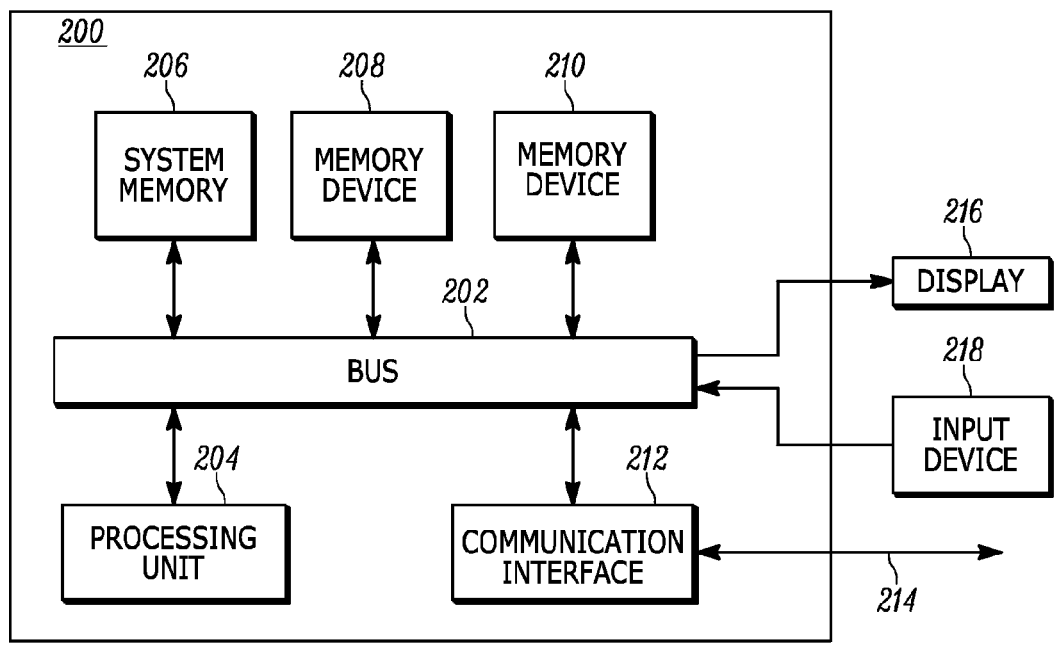
FIG. 3 is a schematic block diagram illustrating an exemplary system of hardware components capable of implementing examples of the systems and methods of the invention.

FIG. 3 is a schematic block diagram illustrating an exemplary system 200 of hardware components capable of implementing examples of the systems and methods disclosed in FIGS. 1 and 2, such as the system 150 illustrated in FIG. 2. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a system control for monitoring and controlling a quantum computing system. Computer executable logic for implementing the system control 126 resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can include either a single medium or multiple non-transitory media operatively connected to the processing unit 204.

Administration and Formulation of Tumor-Targeted Photoactivatable Immunoconjugates In some embodiments, the tumor-targeted photoactivatable immunoconjugate is administered in a pharmaceutically acceptable carrier, e.g., an aqueous carrier. A variety of carriers can be used, e.g., buffered saline and the like. These solutions are sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected.

Administration of the tumor-targeted photoactivatable immunoconjugate for in vivo imaging of a tissue, an organ or a full body can include a) providing a pharmaceutical formulation comprising the tumor-targeting photoactivatable immunoconjugate and a pharmaceutically acceptable excipient and wherein the formulation is suitable for administration as a tumor-targeted photoactivatable immunoconjugate and the immunoconjugate is present in a detectably effective amount; b) providing an imaging device (i.e., an fluorescent imaging device); c) administering the pharmaceutical formulation in an amount sufficient to generate the tissue or body image; and d) imaging the distribution of the pharmaceutical formulation of step a) with the imaging device, thereby imaging the tissue, organ or body.

Dosage depends on various factors, including the amount of the photoactivatable compound administered, the wavelength of the photoactivating light, the intensity of the photoactivating light, and the duration of illumination by the photoactivating light. Thus, the dose of tumor-targeted photoactivatable immunoconjugate can be adjusted to a therapeutically effective dose by adjusting one or more of these factors. Such adjustments are within ordinary skill in the art.

The dosage of the photoactivatable immunoconjugate compositions can vary from about 0.01 mg/m$^2$ to about 500 mg/m$^2$, preferably about 0.1 mg/m$^2$ to about 200 mg/m$^2$, most preferably about 0.1 mg/m$^2$ to about 10 mg/m$^2$. Ascertaining dosage ranges is well within the skill of one in the art. For example, in phase three clinical studies, IMC-C225 loading in human patients was between 100-500 mg/m$^2$, and maintenance was between 100-250 mg/m$^2$. Waksal, H. W., Cancer Metastasis Rev, 18, 427-36 (1999). The dosage of tumor-targeted immunoconjugate compositions can range from about 0.1 to 10 mg/kg. Methods for administering immunoconjugates are known in the art, and are described, for example, in U.S. Pat. Nos. 6,703,020, 7,489,029 and 8,846,002. Such dosages may vary, for example, depending on whether multiple administrations are given, tissue type and route of administration, the condition of the individual, the desired objective and other factors known to those of skill in the art. For instance, the concentration of scFv typically need not be as high as that of native antibodies in order to be therapeutically effective. Administrations can be conducted infrequently, or on a regular weekly basis until a desired, measurable parameter is detected, such as diminution of disease symptoms. Administration can then be diminished, such as to a biweekly or monthly basis, as appropriate.

The pharmaceutical compositions of the invention can be delivered by any means known in the art systematically (e.g. intravenously), regionally or locally (e.g. intra- or peritumoral or intracystic injection, e.g. to image bladder cancer) by e.g. intraarterial, intratumoral, intravenous (iv), parenteral, intrapneural cavity, topical, oral or local administration, as sub-cutaneous intra-zacheral (e.g. by aerosol) or transmucosal (e.g. voccal, bladder, vaginal, uterine, rectal, nasal, mucosal), intra-tumoral (e.g. transdermal application or local injection). For example, intra-arterial injections can be used to have a "regional effect", e.g. to focus on a specific organ (e.g. brain, liver, spleen, lungs).

The present invention is illustrated by the following example. It is to be understood that the particular example, materials, amounts, and procedures are to be interpreted broadly in accordance with the scope and spirit of the invention as set forth herein.

EXAMPLE

Example 1

Selective Treatment and Monitoring of Disseminated Cancer Micrometastases In Vivo Using Dual-Function, Activatable Immunoconjugates Drug-resistant micrometastases that escape standard therapies often go undetected until the emergence of lethal recurrent disease. Here the inventors show that it is possible to treat microscopic tumors selectively using an activatable immunoconjugate. The immunoconjugate is composed of self-quenching, near infrared chromophores loaded onto a cancer cell-targeting antibody. Chromophore phototoxicity and fluorescence are activated by lysosomal proteolysis, and light, after cancer cell internalization, enabling tumor-confined photocytotoxicity and resolution of individual micrometastases. This unique approach not only introduces a therapeutic strategy to help destroy residual drug-resistant cells but also provides a sensitive imaging method to monitor micrometastatic disease in common sites of recurrence. Using fluorescence microendoscopy to monitor immunoconjugate activation and micrometastatic disease, the inventors demonstrate these concepts of 'tumor-targeted, activatable photoimmunotherapy' (taPIT) in a mouse model of peritoneal carcinomatosis. By introducing targeted activation to enhance tumor selectively in complex anatomical sites, this study offers new prospects for catching early recurrent micrometastases and for treating occult disease.

The embodiment described in this example is fluorescence microendoscopy (optical imaging) combined with a tumor-targeted, activatable probe (an advanced molecular imaging contrast agent) and bioimage informatics (an image processing workflow) for accurate recognition (93% sensitivity and 93% specificity) of micrometastases as small as 30 μm. This embodiment was demonstrated in a clinically-motivated mouse model of disseminated, micrometastatic ovarian cancer. As proof-of-concept, a monochromatic, wide-field fluorescence microendoscope was used to image an activatable immunoconjugate that targets epidermal growth factor receptor (EGFR) to enable high-contrast imaging (and selective treatment) of multifocal cancer micrometastases spread throughout the peritoneal cavity that overexpress EGFR protein (the molecular target). In this embodiment, a second layer of tumor selectivity was achieved by cellular processing (lysosomal proteolysis) and activation upon internalization of the immunoconjugate into the cancer cells. EGFR-targeting limits entry of the immunoconjugate to cancer cells overexpressing this target molecule, and the chromophores loaded onto the immunoconjugate are activated into an "ON" state (by releasing fluorescence and photodynamic quenching) upon cellular internalization and proteolysis. Finally, a bioimage infomatics workflow was newly developed and rigorously validated by comparing quantification of micrometastatic burden using this method for optical biopsy versus an ex vivo histopathologic and biochemical assays (quantitative reverse transcription-polymerase chain reaction, qRT-PCR) performed on biopsied tissue specimens precisely matched to the in vivo images.

Results

Figure 4:
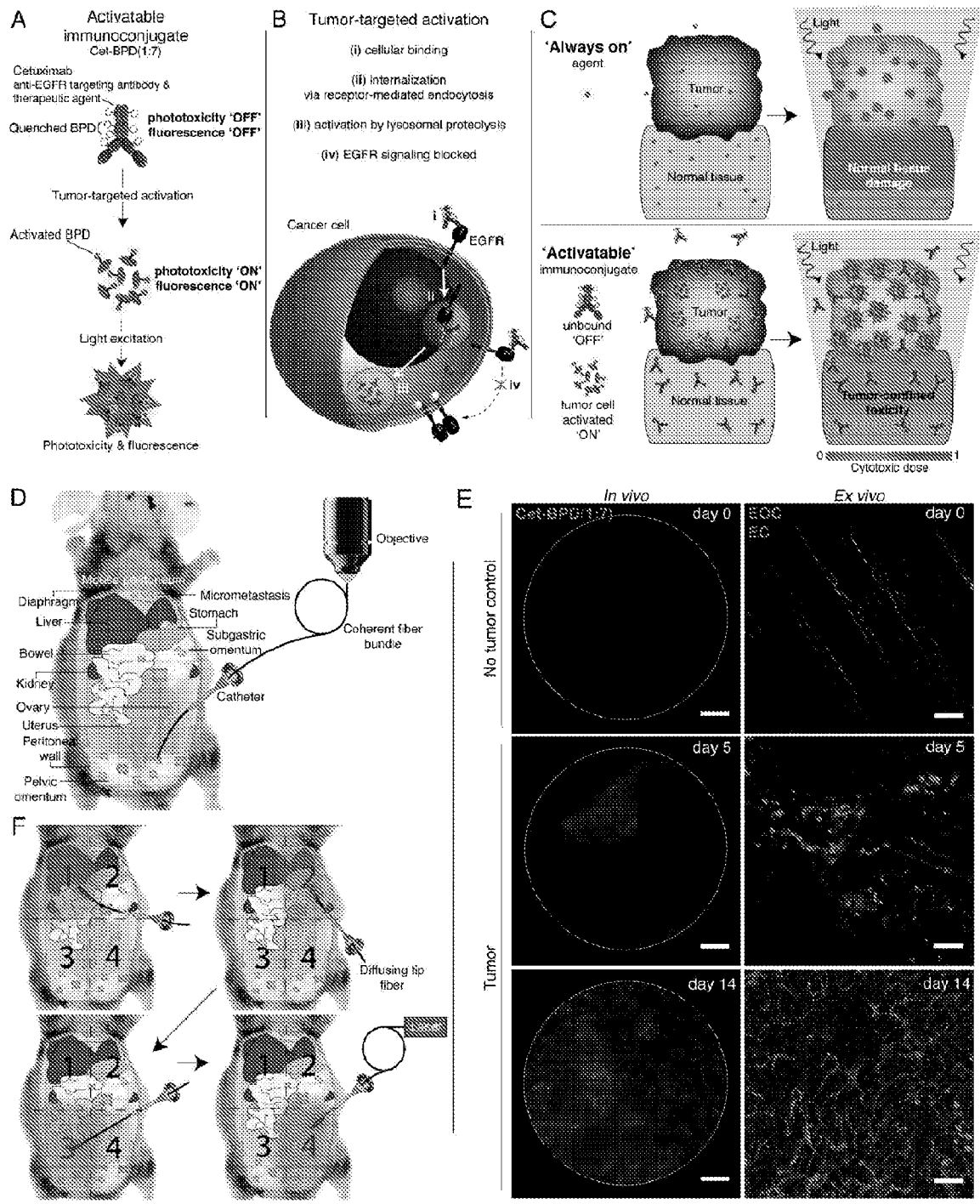
FIG. 4 (A-C) provides images illustrating concepts of tumor-targeted, activatable photoimmunotherapy (taPIT) and longitudinal monitoring of micrometastases in vivo. (A) Cet-BPD—a dual-function, activatable immunoconjugate for both taPIT and monitoring of micrometastases—consists of multiple BPD molecules conjugated to each cetuximab molecule. The BPD molecules remain self-quenched until EGFR-binding and cellular internalization. (B) Schematic of Cet-BPD intracellular activation. (C) TaPIT enables tumor-confined phototoxicity while 'always on' agents and immunoconjugates result in nonspecific damage to normal tissues. (D) Mouse model of micrometastatic epithelial ovarian cancer (EOC) and fluorescence microendoscopy schematics. (E) Left: in vivo fluorescence microendoscopy of control no tumor and EOC mice on days 5 and 14 post-tumor inoculation. Right: corresponding ex vivo immunofluorescence images show human EOC and mouse endothelial (EC) cells stained with anti-CK8 and -CD31 antibodies, respectively. Scale bars are 100 µm. Note that all images in this report are displayed on a linear scale deliberately without saturation. Non-linear, saturated image display appears to show higher contrast, but such a representation is not quantitative. (F) Schematic of intraperitoneal Cet-BPD photoactivation using a diffusing tip fiber and scattering media to enable efficient, targeted wide-field treatment of micrometastatic disease spread throughout the abdominal cavity by stepwise irradiation of each quadrant within the cavity.

Quantitative fluorescence microendoscopy-guided taPIT platform. The inventors developed an integrated therapeutic and imaging platform using quantitative fluorescence microendoscopy with dual-function, activatable immunoconjugates to treat and visualize micrometastatic nodules in vivo (FIG. 4). First the inventors quantified tumor-targeted activation of the immunoconjugate in vivo (FIG. 5) as well as micrometastasis imaging accuracy (FIG. 6). To optimize treatment selectivity and dosimetry, the inventors applied longitudinal fluorescence microendoscopy to characterize immunoconjugate pharmacokinetics and tumor-selectivity dynamics in vivo (FIG. 7). Next, the inventors demonstrated that tumor-targeted, activation reduces non-target phototoxicity compared to a number of control agents—including unconjugated, 'always on' agents—while realizing selective destruction of micrometastases in vivo (FIG. 8). Finally, the inventors confirmed micrometastasis imaging accuracy by histopathologic grading of specimens ex vivo co-registered with in vivo fluorescence microendoscope images (FIG. 9).

The immunoconjugate used in this study is comprised of FDA-approved photodynamic and anti-EGFR therapeutic agents (FIG. 4A and FIG. 11) previously demonstrated to reduce metastatic EOC burden synergistically when used in combination as unconjugated, individual agents. del Carmen M G et al., J Natl Cancer Inst 97:1516-1524 (2005). Cetuximab, an anti-EGFR monoclonal antibody (mAb), targets cancer cells overexpressing EGFR. EGFR is an important molecule for targeting cancer cells that displays elevated expression in up to 70% of EOCs (Psyrri A et al., Clin Cancer Res 11:8637-8643 (2005)) and in many other carcinomas. Mendelsohn J, Baselga J., J Clin Oncol 21:2787-2799 (2003). Although EGFR-targeting is the focus here, immunoconjugate synthesis, imaging and taPIT are all generalizable such that a variety of targeting molecules for other tumor antigens may be applied. Benzoporphyrin derivative (BPD) is a clinically-approved NIR photoactivable and cytotoxic chromophore that undergoes electronic excited singlet state quenching upon antibody conjugation—as described by Savellano et al. (Savellano M D, Hasan T, Photochem Photobiol 77:431-439 (2003))—with increasing self-quenching in parallel with higher loading ratios. This quenching phenomenon increases the tumor specificity when optimally designed, however, excess BPD loading results in the loss of cancer cell-specific delivery. In a series of chemical synthesis and in vitro cell culture studies, the inventors previously identified an optimal conjugation ratio of ~7 BPD molecules per mAb molecule, Cet-BPD(1:7), as a strongly quenched (7-fold) and cancer cell-specific construct that retains the biological activity of cetuximab. Abu-Yousif A O et al., Cancer Letters 321:120-127 (2012). These in vitro studies suggest that, like cetuximab, Cet-BPD is trafficked to lysosomes as part of the EGFR internalization and degradation pathway where more than half of the Cet-BPD immunoconjugates release BPD resulting in de-quenching and activation of both BPD phototoxicity and fluorescence emission in cell culture. Savellano M D, Hasan T., Clin Cancer Res 11:1658-1668 (2005). Note that the immunoconjugate has a minimal, but non-negligible, baseline level of phototoxicity and fluorescence emission in the quenched state.

Although these prior in vitro studies offered promise, the inventors sought to test the true measures of taPIT and activatable tumor imaging—enhancement of micrometastasis treatment selectivity and imaging accuracy in vivo. The inventors hypothesized that Cet-BPD could serve as both a molecular-targeted, activatable therapeutic agent and imaging probe for selectively treating and monitoring microscopic tumor deposits in vivo. Here the inventors show that—in vivo—Cet-BPD is selectively activated within micrometastases and imparts selective tumor cytotoxicity upon NIR irradiation.

In vivo Cet-BPD imaging was achieved using a custom-built microendoscope (Zhong W et al., Br J Cancer 101:2015-2022 (2009)) to detect occult micronodules in a mouse model of EOC characterized by disseminated metastases (FIG. 4E). The microendoscope probe enters the peritoneal cavity via a 14-gauge catheter traversing the abdominal wall (FIG. 4D) without the need for surgery or sutures. In vivo fluorescence microendoscopy prior to (day 0, no tumor control) and at various days following tumor inoculation (days 5 and 14, tumor) show the specificity of Cet-BPD fluorescence for micrometastases (FIG. 4E). To verify the presence and absence of tumor in these mice the inventors applied an anti-human cytokeratin 8 (CK8) immunostain specific for human EOC cells and also stained microvasculature (anti-mouse PECAM-1, CD31), which is initially absent but becomes tortuous after neoangiogenesis within advanced EOC nodules (FIG. 4E and FIG. 11).

Figure 5A:
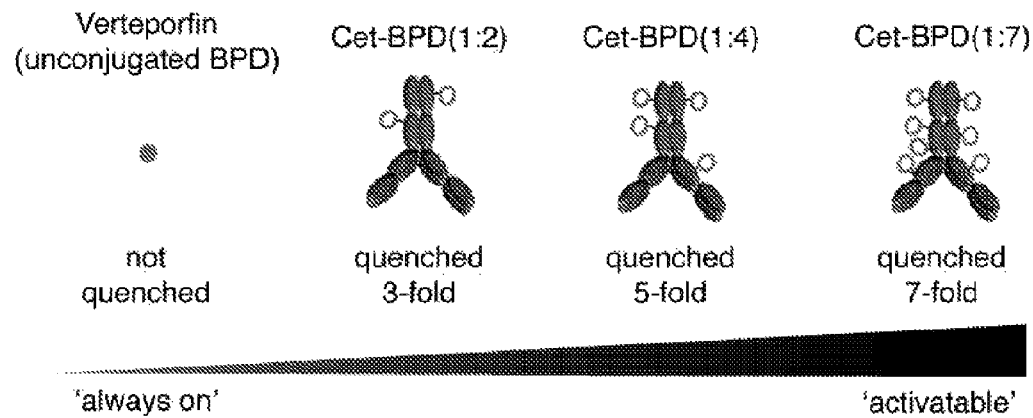
FIG. 5 (A-E) provides graphs and images showing In vivo Cet-BPD activation in tumors versus non-target tissues. (A) Constructs with varying BPD quenching efficiencies. (B) In vivo fluorescence microendoscopy of Cet-BPD(1:7) (1.4 mg cetuximab; n=4 mice, 160 fields) shows reduced nonspecific fluorescence compared to Cet-BPD(1:2) (1.4 mg cetuximab; n=3 mice, 120 fields) in control, no tumor mice (mean±s.e.m., *P<0.05 *P<0.001 **P<0.0001, two-tailed unpaired t-test). (C) Spectrally unmixed BPD fluorescence and autofluorescence (gray scale) from hyperspectral fluorescence images of the bowel (outlined in each image; see also images of the entire peritoneal cavity, 2 hours after verteporfin or 48 hours after Cet-BPD(1:7) administration. Intensity scales are matched for no tumor control and EOC mice (day 23). (D) Quantification of BPD in peritoneal tissues of EOC mice (day 10) by extraction. (E) Tumor-to-tissue ratios for Cet-BPD(1:7) (n=15 mice; binned data from 8, 12 and 24 hours post-administration to reduce noise) versus verteporfin (n=10 mice; binned data from 2 and 4 hours post-administration) calculated from (D) (mean±s.e.m., *P<0.05 P<0.01 *P<0.001 ****P<0.0001, two-tailed unpaired t-test).
Figure 5B:
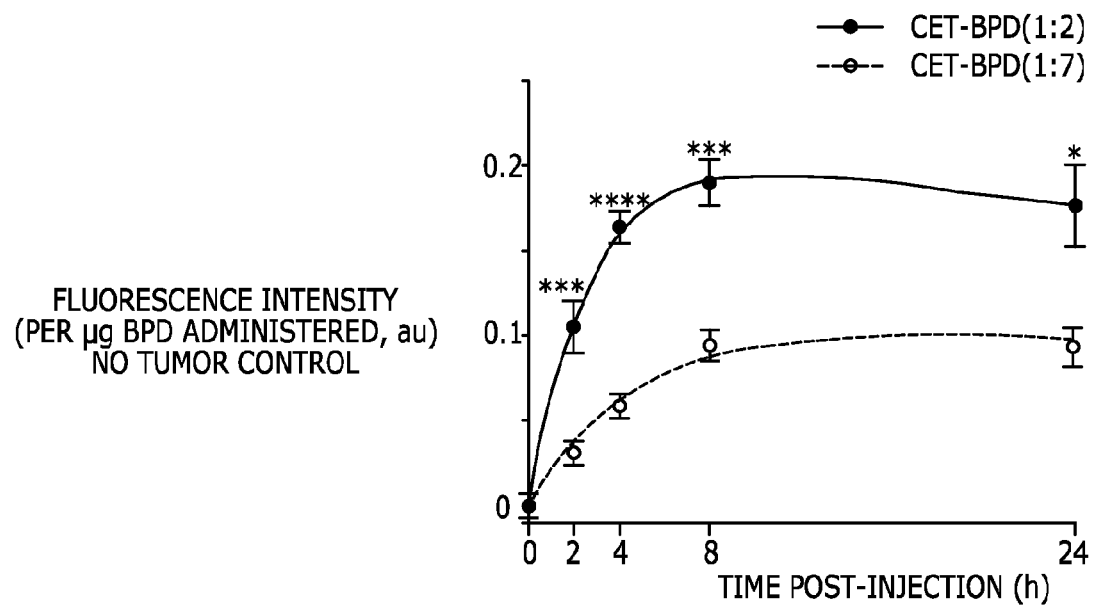

Tumor-selective immunoconjugate activation. To demonstrate tumor-specific activation of Cet-BPD in vivo, the inventors used quantitative imaging methods validated by conventional techniques. TaPIT toxicity, Cet-BPD imaging and Cet-BPD tissue extraction studies were conducted using constructs with varying degrees of BPD quenching (FIG. 5A). Cet-BPD fluorescence was investigated at various scales, from macroscopic biodistribution to microscopic intratumoral localization. These results confirmed that Cet-BPD(1:7) largely remains quenched in normal tissue in vivo. Cet-BPD(1:7) displayed approximately two-fold less non-specific fluorescence than Cet-BPD(1:2) per BPD molecule administered (FIG. 5B), in agreement with the 2.3-fold increased quenching strength of Cet-BPD(1:7) previously characterized in vitro. Savellano M D, Hasan T, Photochem Photobiol 77:431-439 (2003).

Figure 5C:
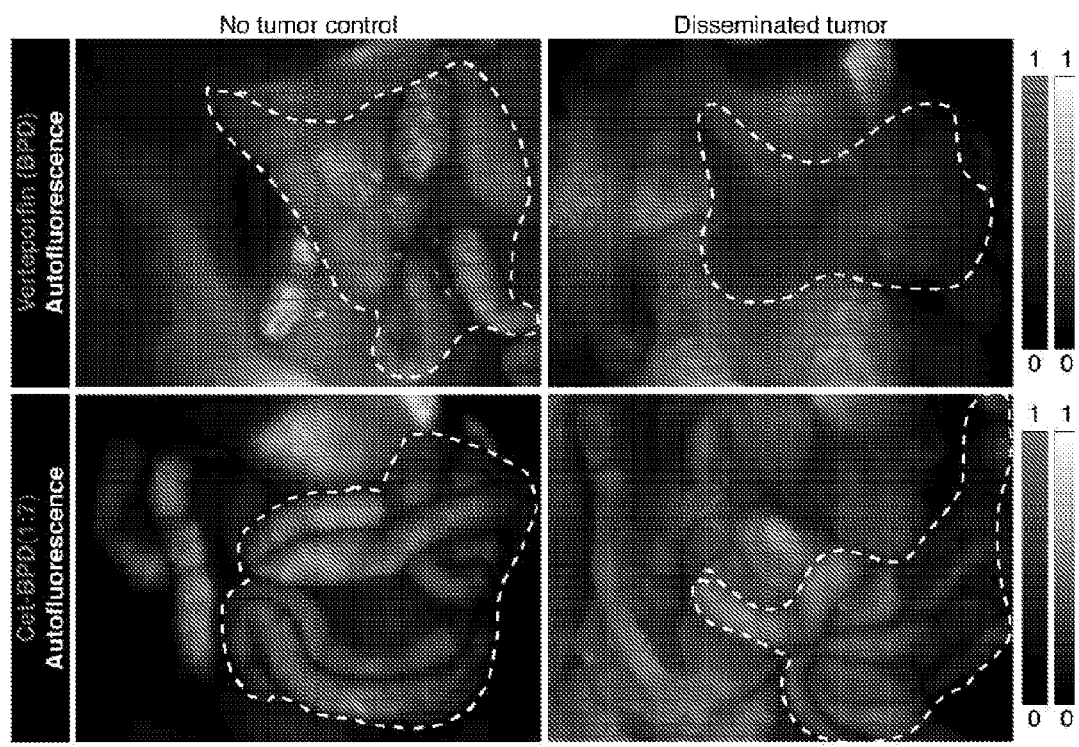
Figure 5D:
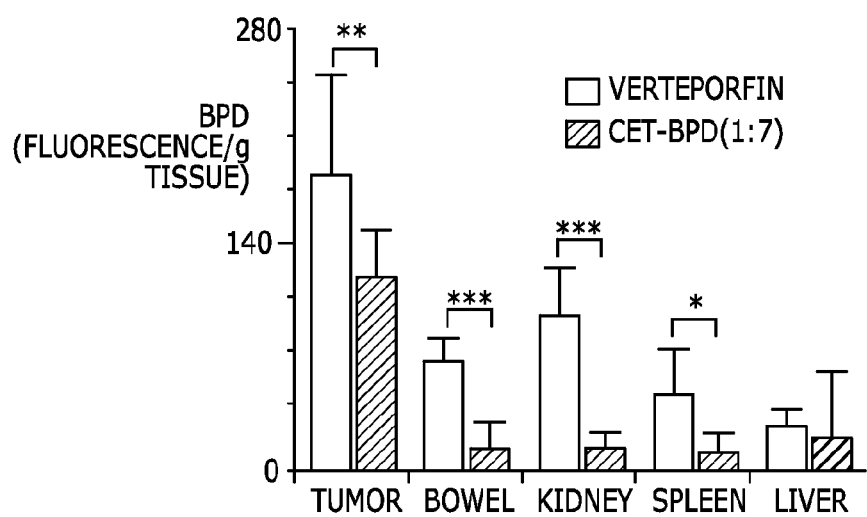
Figure 5E:
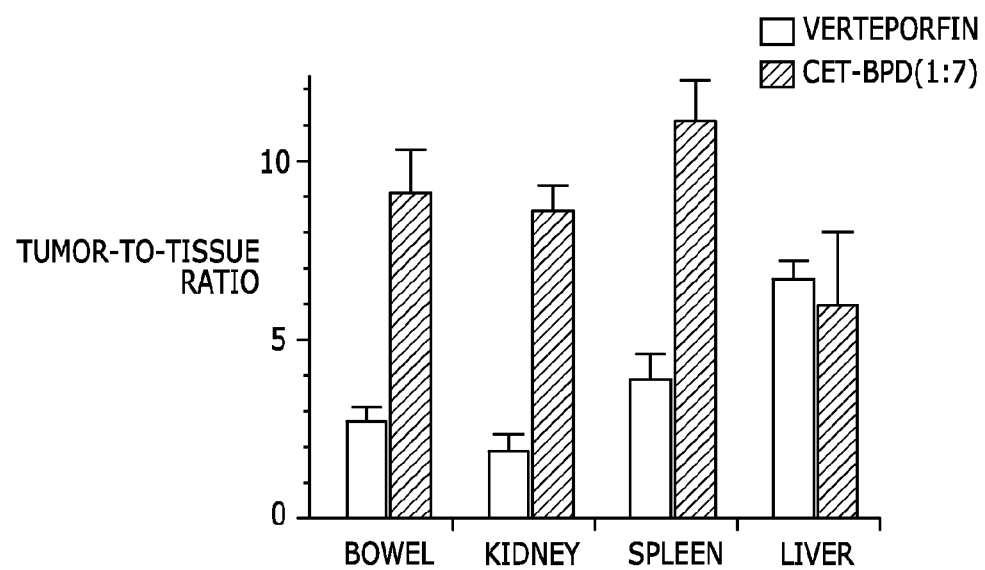

The inventors next investigated activation of Cet-BPD in multi-focal tumors studding vital peritoneal organs. In situ imaging-based biodistribution studies at fixed time points revealed enhanced tumor specificity of activatable Cet-BPD (1:7) compared to verteporfin, the present clinical, liposomal formulation of 'always on' BPD. Hyperspectral fluorescence imaging of the peritoneal cavity—at the macroscopic scale—was validated by Cet-BPD extraction studies from pulverized tissues at matched time points. These data indicate low tumor selectivity for verteporfin (FIG. 5C-E); e.g., verteporfin has a tumor-to-bowel ratio of 2.7 (FIG. 5D). In contrast, Cet-BPD(1:7) has a much lower signal in the bowel and other sensitive organ tissues than verteporfin, achieving a tumor-to-bowel ratio of 9.2 (FIG. 5C-E). However, this is a conservative estimate as the Cet-BPD signal in non-tumor tissue is at the lower detection limit Fitting the pharmacokinetic data to a model suppresses noise and indicates tumor-to-bowel ratios of 2.8 for verteporfin and 18.6 for Cet-BPD. This improved tumor selectivity is also seen in the hyperspectral fluorescence images following spectral deconvolution. The bowel is outlined in each image to highlight decreased BPD signal for Cet-BPD(1:7) compared to verteporfin (FIG. 5C). Thus, activatable immunoconjugates for taPIT significantly reduce bowel toxicity the major obstacle in the clinical translation of photodynamic therapy of intraperitoneal metastases.

Figure 6A:
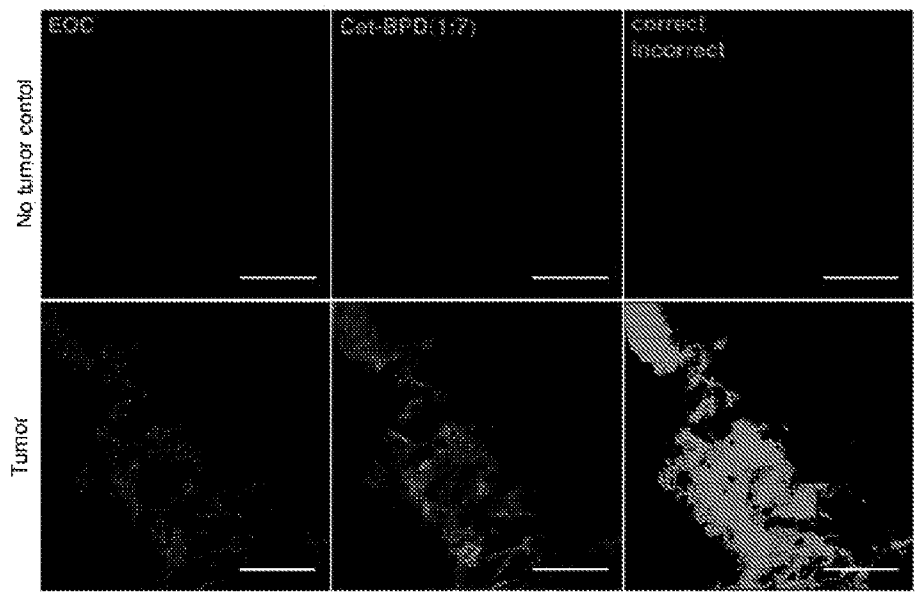
FIG. 6 (A-E) provides graphs and images showing microscale-localization of activated Cet-BPD in vivo. (A) Cet-BPD fluorescence confocal image mosaics of freshly excised tissue from control no tumor and EOC mice. The locations of human EOC cells (anti-human CK8 stain) are also shown for comparison, as well as pixels correctly and incorrectly classified as tumor based on the optimal Cet-BPD intensity threshold shown in (B). (B) The green and red curves represent the percentage of pixels correctly classified and those incorrectly classified as tumor, respectively, versus a range of potential Cet-BPD fluorescence intensity thresholds. A dotted black line indicates the optimal threshold for tumor classification. (C) ROC analysis of Cet-BPD tumor selectivity Minimum tumor size of 30 µm: 93% sensitivity and 93% specificity, ROC area under the curve (AUC)=0.961, n=12 mice (296 fields). (D, E) Maximum intensity projections of 3D confocal images (D) and quantitative analysis (E) demonstrate colocalization (mean±s.e.m.) of activated Cet-BPD with EOC cells but not with EC cells (anti-CD31 stain), n=7 mice (262 optical sections, ****P<0.0001, two-tailed unpaired t-test). Scale bars are 1 mm in (A) and 100 µm in (D).
Figure 6B:
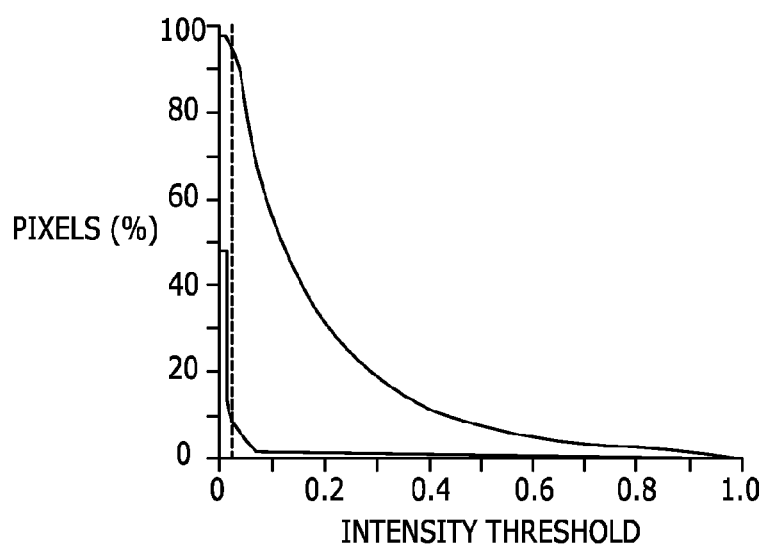
Figure 6C:
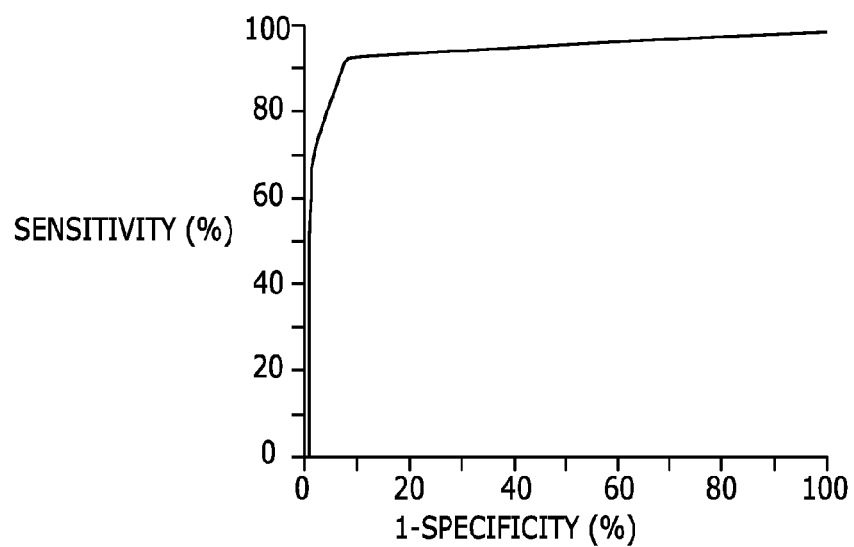
Figure 6D:
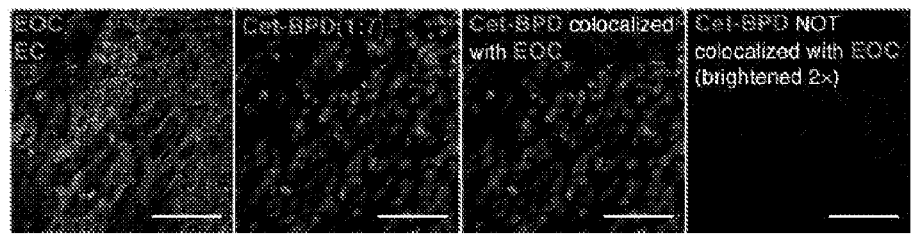
Figure 6E:
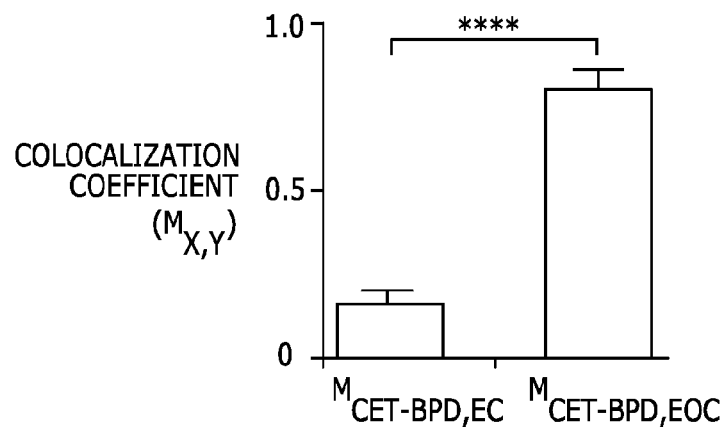

To quantify the three-dimensional (3D) microscale localization of activated Cet-BPD immunoconjugates within micrometastases, the inventors performed confocal microscopy on freshly excised tissues. Immunostains for human EOC cells, mouse EC cells and mouse immune cells were applied ex vivo. The inventors were able to detect clusters of EOC cells with BPD fluorescence in tissues excised from tumor bearing mice, but not in healthy mice (FIG. 6A). To assess the tumor-specificity of Cet-BPD activation quantitatively, the inventors designed a pixel-by-pixel tumor classification test based on a Cet-BPD fluorescence intensity threshold from which the inventors determined Cet-BPD sensitivity (fraction EOC pixels correctly identified) and specificity (1−fraction EOC pixels incorrectly identified) (FIG. 6B). The optimal threshold, determined by receiver operating characteristic (ROC) analysis (FIG. 6C), attained 93% sensitivity and 93% specificity for micrometastases as small as 30 µm. Furthermore, high-magnification confocal depth-scans of micrometastases revealed that 81% of Cet-BPD fluorescence colocalizes with EOC cells (FIGS. 6D and E).

To address the question of inflated tumor selectivity due to a lack of cross-reactivity with basal mouse EGFR levels, the inventors investigated Cet-BPD binding to both mouse and human EGFR. The EGFR binding specificity, cellular internalization and activation profiles of Cet-BPD(1:7) are similar for murine and human cells. Furthermore, previous in vitro studies have shown that Cet-BPD is highly selective to cancer cells overexpressing EGFR surface molecules with 20-fold less accumulation in low EGFR-expressing cells. Hence, the tumor selectivity achieved by Cet-BPD is due to tumor-targeted activation.

Figure 11A:
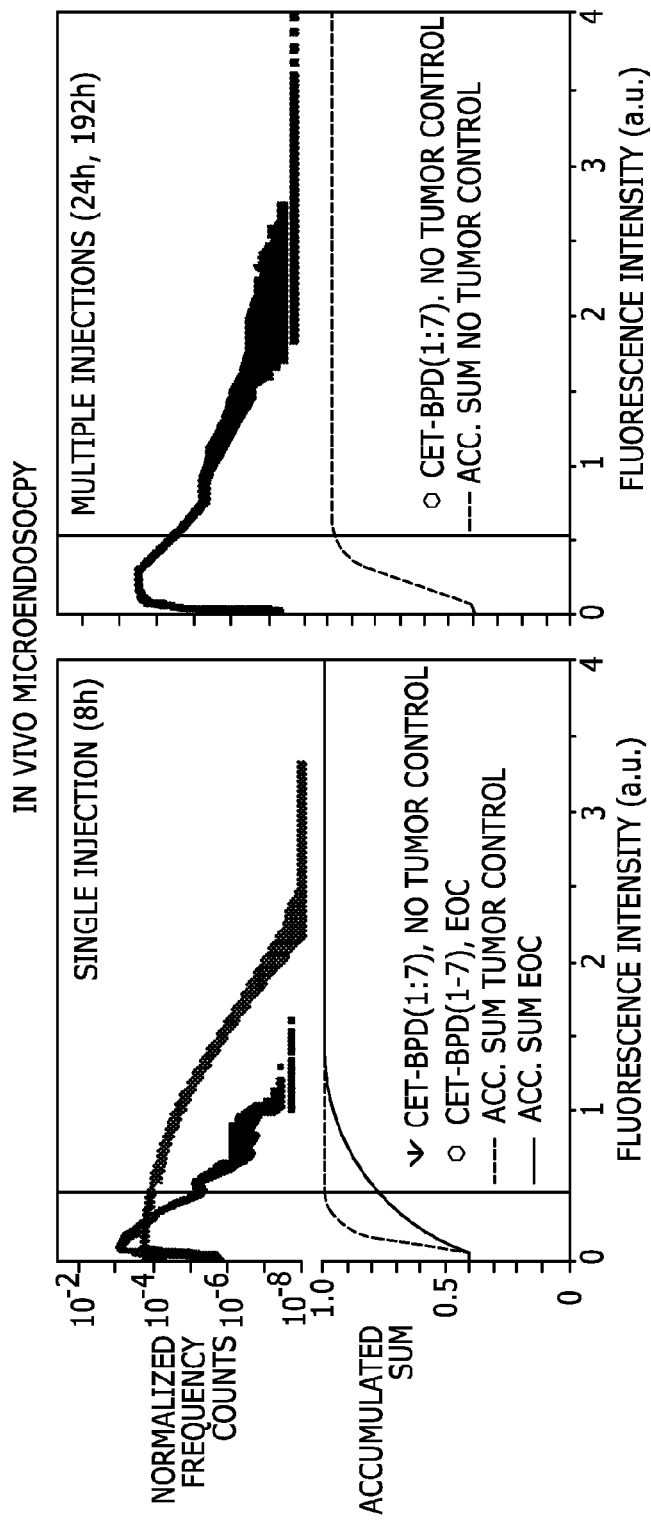
Figures 1, 11B:
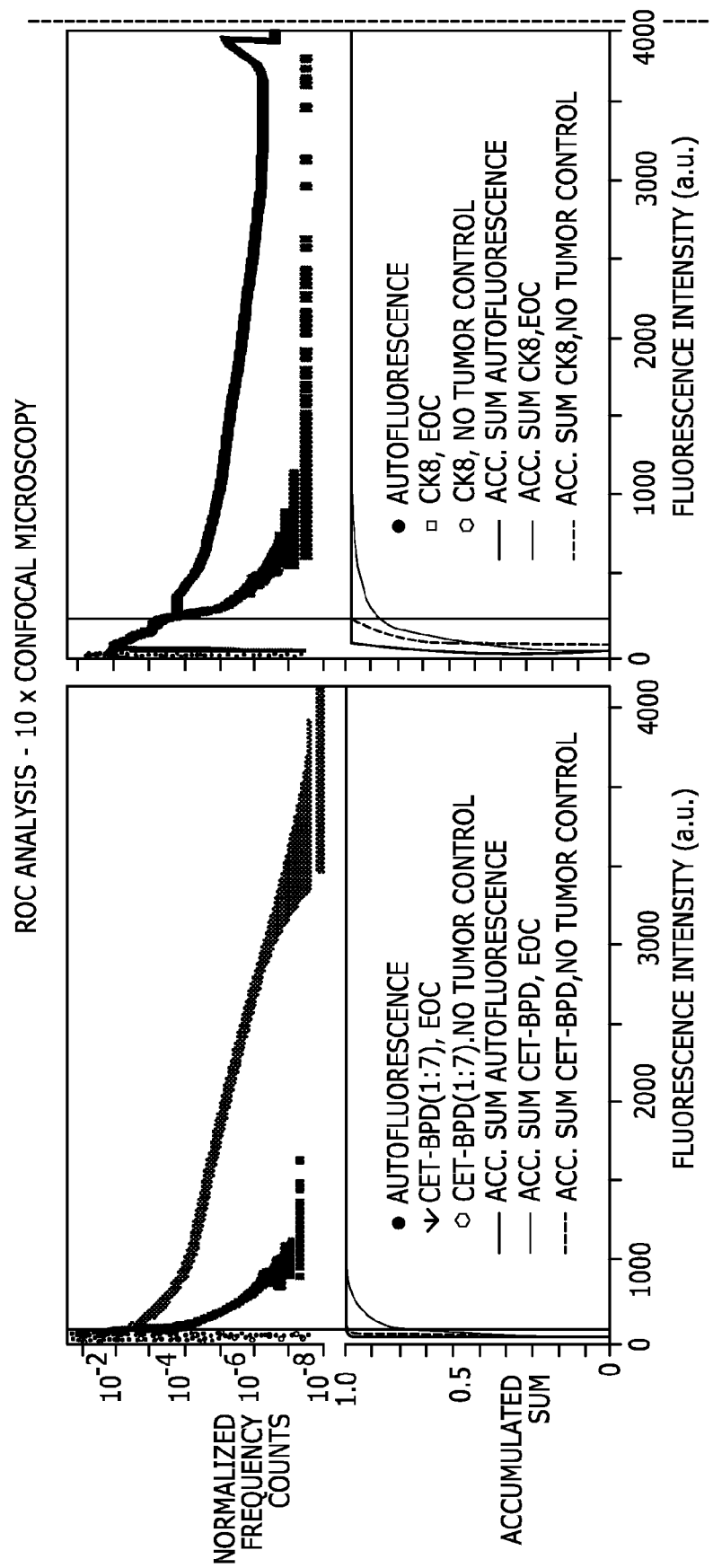
Figures 2, 11B:
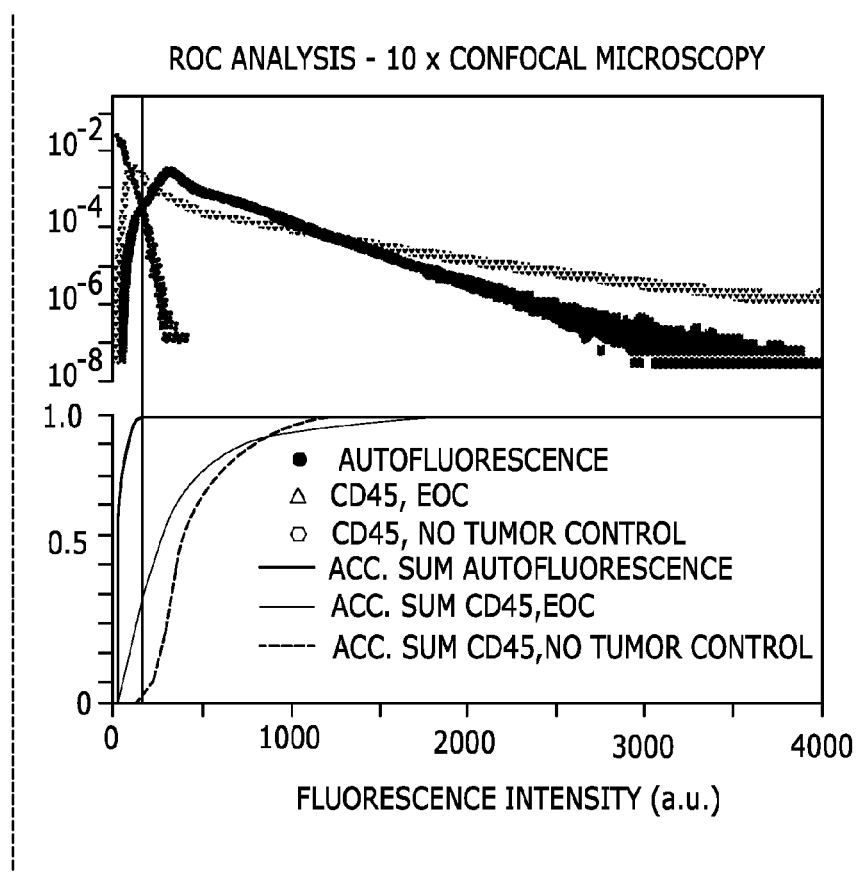
Figures 1, 11C:
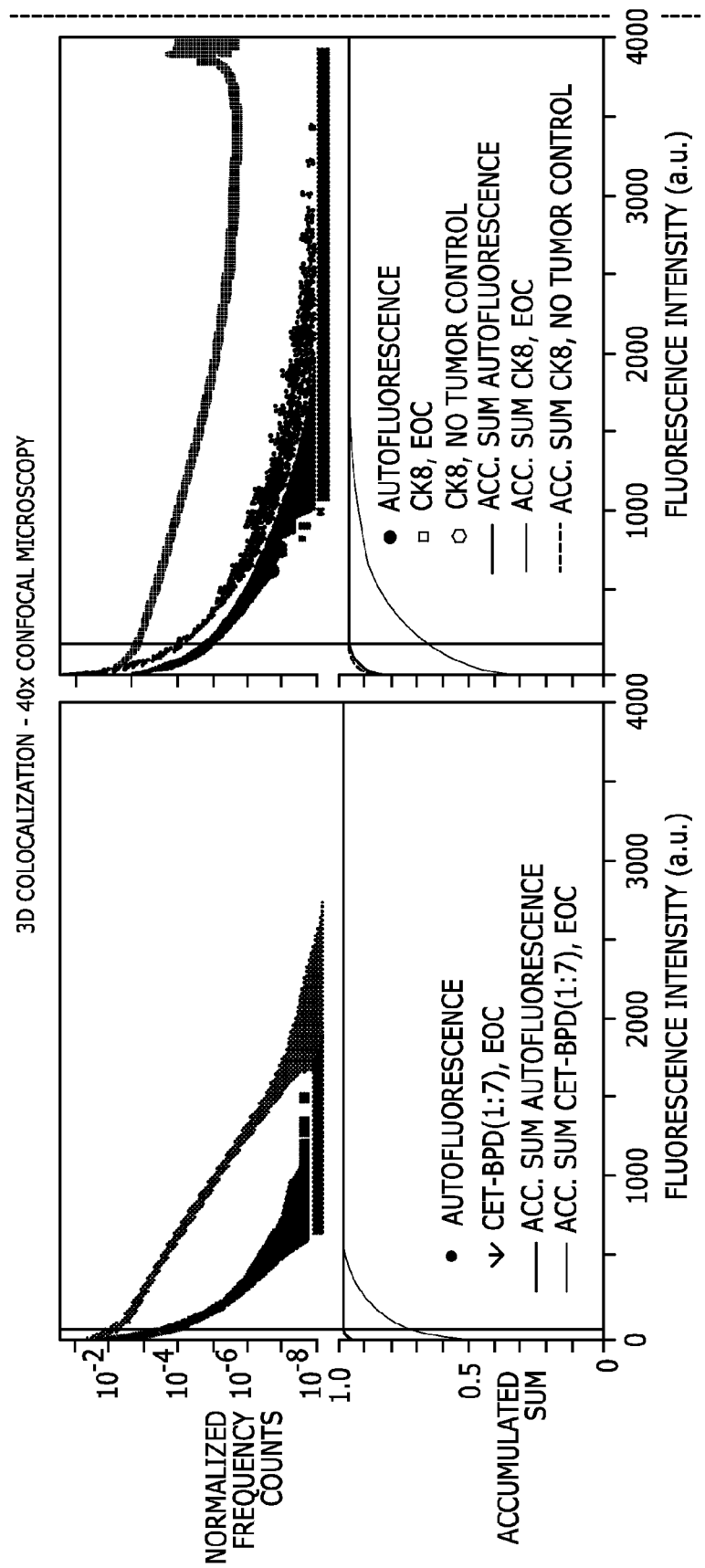
Figures 2, 11C:
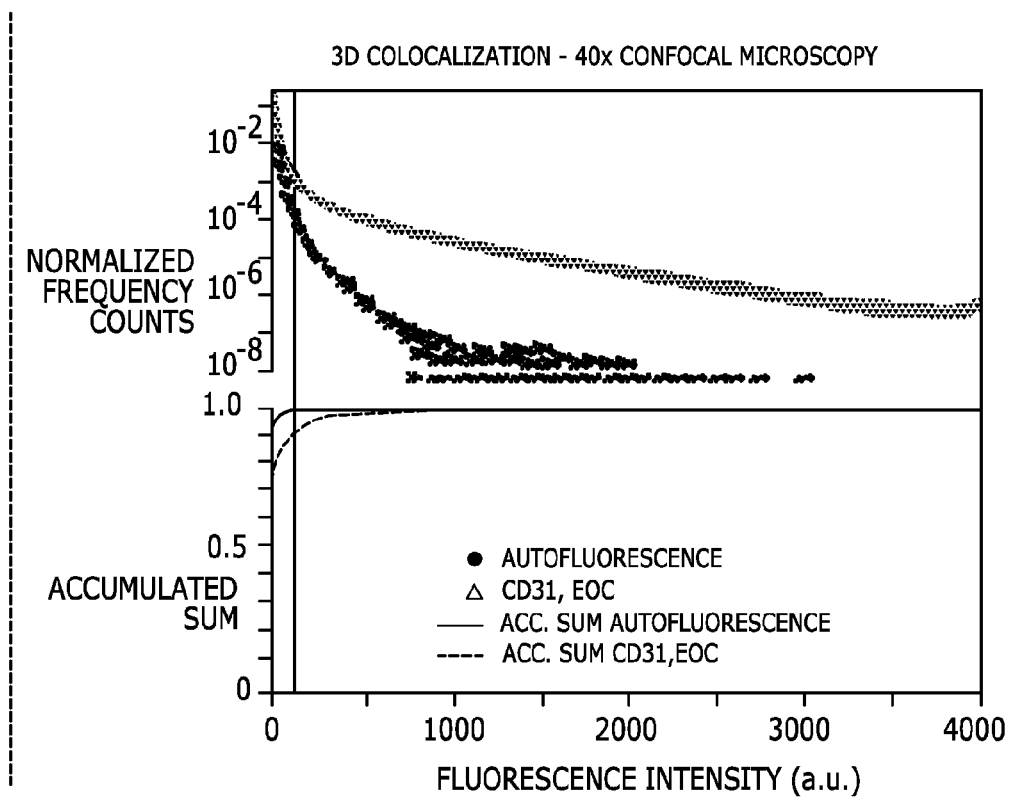

Longitudinal imaging of immunoconjugate pharmacokinetics. Characterization of immunoconjugate pharmacokinetics and tumor selectivity dynamics enables determination of optimal time points for micrometastasis imaging and for NIR irradiation to perform taPIT. The inventors developed in vivo longitudinal imaging of immunoconjugate pharmacokinetics using fluorescence microendoscopy. In contrast to the biodistribution data presented above—where a separate group of mice was sacrificed at each time point—this approach enables longitudinal monitoring of individual mice, which significantly reduces both the use of animals and labor to characterize pharmacokinetics. To expedite interpretation of the acquired fluorescence microendoscopy images, the inventors developed a rapid batch image processing workflow capable of automated and objective interpretation of the raw images. The workflow incorporates mean autofluorescence subtraction, pharmacokinetics-informed tumor thresholding and correction factors for quantitative tumor burden imaging (FIG. 10) with >95% rejection of nonspecific fluorescence background for pixel-by-pixel tumor recognition (FIG. 11A).

FIG. 10 shows the process used for longitudinal micrometastatic burden quantification by in vivo fluorescence microendoscopy using an image analysis workflow that integrates multiple experiments to inform batch processing of the data. The workflow holds promise for development into a bioimage informatics platform, by adoption of a relational database to facilitate hypothesis-driven, unbiased and quantitative analyses of in vivo microendoscopy experiments for optimizing tumor recognition accuracy, drug screening and therapeutic regimen development. Swedlow et al., Science 300:100-102 (2003); Millard et al., Nat Meth 8:487-493 (2011). In step (A), raw images from many experiments are obtained. In step (B), corresponding background and calibration images of water and 1 µM verteporfin in phosphate-buffered saline with 2% TritonX-100, respectively, were collected for each experiment to subtract background (e.g., detector dark current) and to normalize images to a standard for global comparison while also correcting the excitation light profile. In step (C) a binary mask selects pixels within the coherent fiber bundle for analysis using a 5% maximum intensity threshold, followed by an 'erode' operation to avoid including the fiber edges. In step (D), mean autofluorescence was calculated for each tissue site (n=3 mice, 118 fields including no tumor control and EOC mice): 0.039, peritoneal wall; 0.000, pelvic omentum. In step (E), mean autofluorescence subtraction was performed for all images. In step (F), fits to a simple pharmacokinetic (PK) model were carried out for control no tumor and EOC mice to facilitate corrections for residual Cet-BPD during multi-immunoconjugate injection experiments. In step (G), adjustment of the 99.5% background-rejecting, tumor-recognition intensity threshold based on Cet-BPD pharmacokinetics (PK) in non-tumor tissue was carried out. In step (H), selection of tumor objects in images using the tumor-recognition threshold was performed. In step (I), removal of any tumor objects less than 30 µm in dimension based on ROC analysis (FIG. 6). Finally, in step (J), calculation of the integrated tumor fluorescence intensity as a surrogate for micrometastatic burden was performed. The second term subtracts the increased nonspecific fluorescence background following multiple immunoconjugate injections based on Cet-BPD pharmacokinetics (PK). The final term adjusts the tumor fluorescence, based on pharmacokinetic (PK) measurements, for increasing tumor signal following multiple immunoconjugate injections.

Figure 7A:
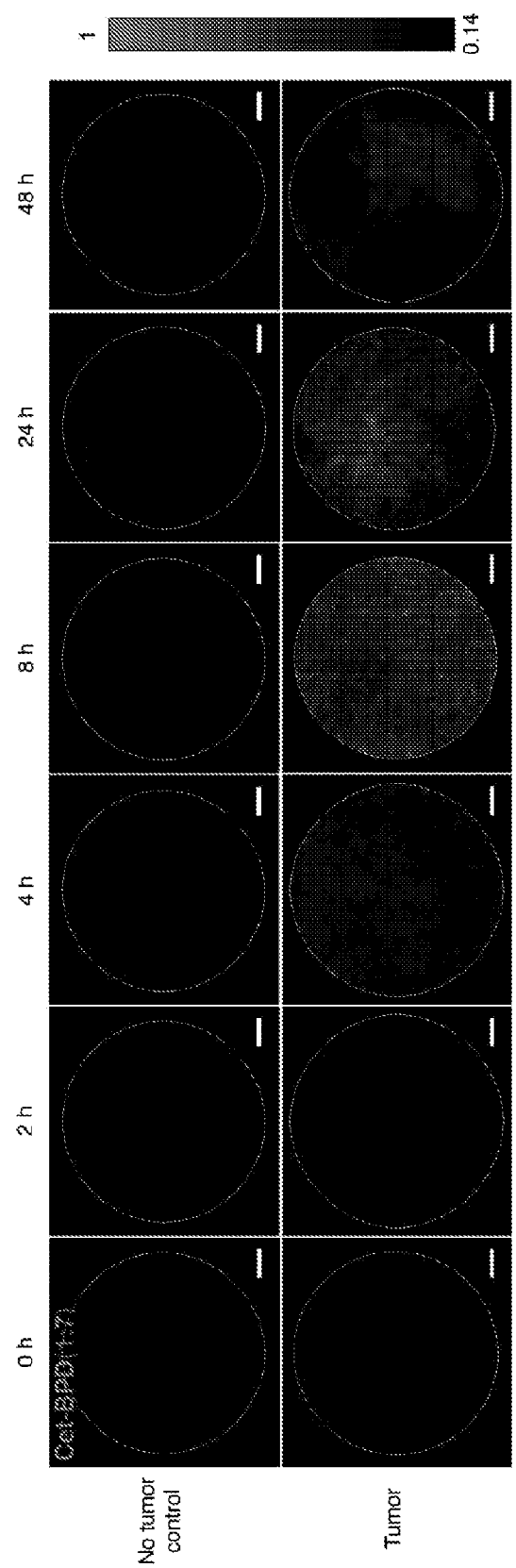
FIG. 7 (A-F) provides graphs and images showing In vivo Cet-BPD tumor selectivity dynamics. (A) Longitudinal in vivo fluorescence microendoscopy shows Cet-BPD(1:7) micrometastasis-specificity 8-24 hours post-administration. Scale bars are 100 µm. (B) Mean (±s.e.m) pharmacokinetic traces for Cet-BPD by fluorescence microendoscopy (40 fields per mouse) and extraction (including multiple tissue sites). The trend lines are fits to a simple pharmacokinetic model (SI Text). Fluorescence microendoscopy Cet-BPD: control, n=4 mice; tumor, n=3 mice. Extraction Cet-BPD (per time point): control, n=5 mice; tumor, n=5 mice (*P<0.05 P<0.01 *P<0.001 **P<0.0001, two-tailed unpaired t-test). (C) Tissue extraction studies validate Cet-BPD pharmacokinetic fluorescence microendoscopy. The plot includes the data in (B) and additional data for verteporfin. (D) Tumor selectivity dynamics by fluorescence microendoscopy for Cet-BPD, Tra-BPD (HER2-targeted mAb) and IgG-BPD (nonspecific, polyclonal antibody). Tra-BPD control, n=3 mice; tumor, n=4 mice. IgG-BPD control, n=4 mice; tumor, n=3 mice. (E) Western blot determination of relative EGFR and HER2 protein expression levels in EOC cells (positive and negative control cell lines are also shown). (F) Mean (±s.e.m.) EOC EGFR expression is higher than that of HER2 by blot densitometry, n=3 replicates (*P=0.00016, two-tailed unpaired t-test).
Figure 7B:
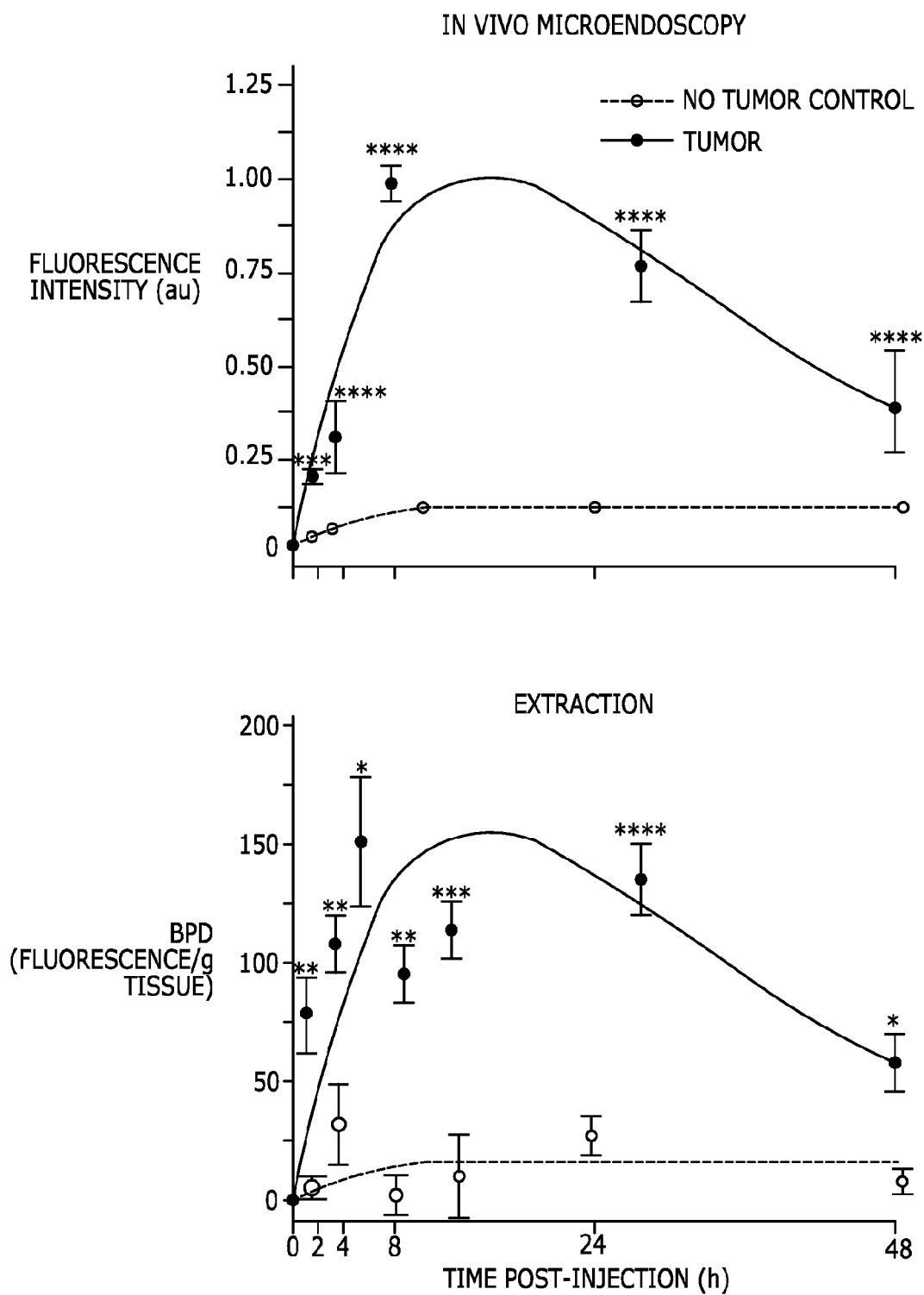
Figure 7C:
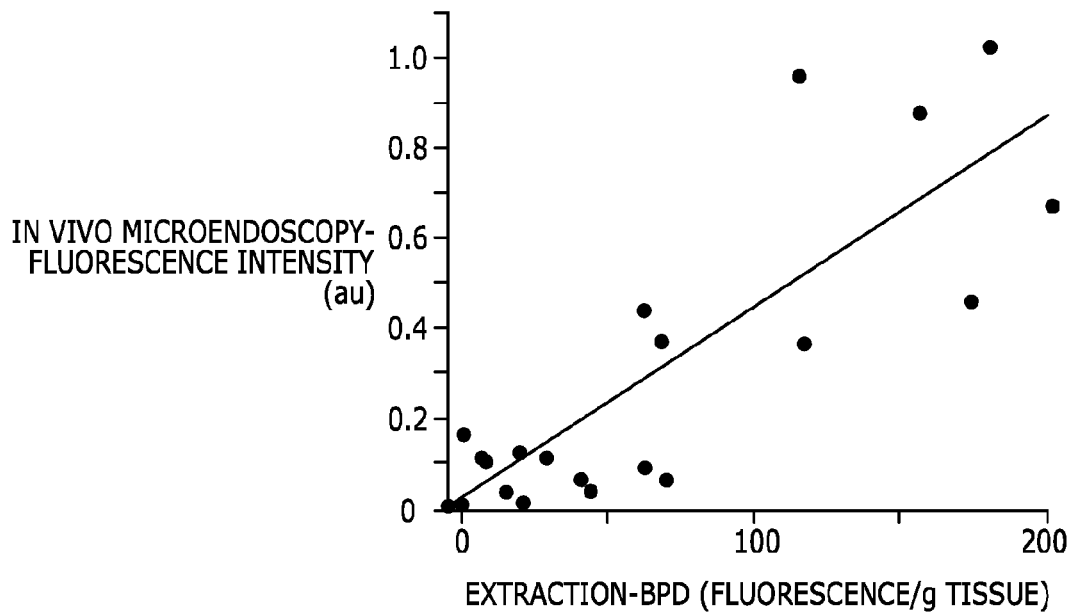
Figure 7D:
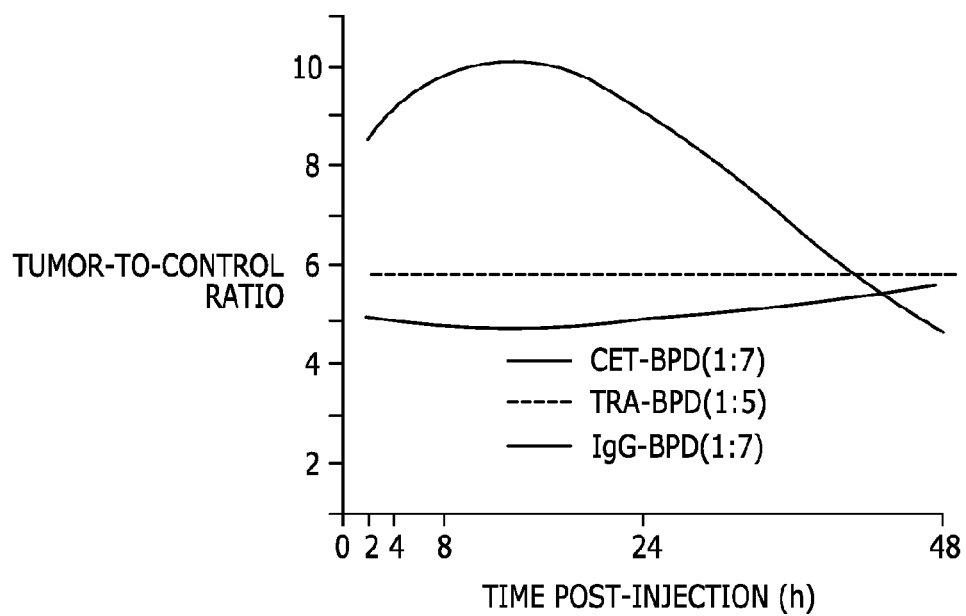
Figure 7E:
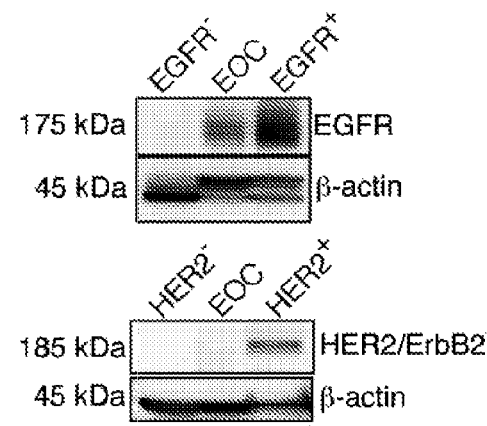
Figure 7F:
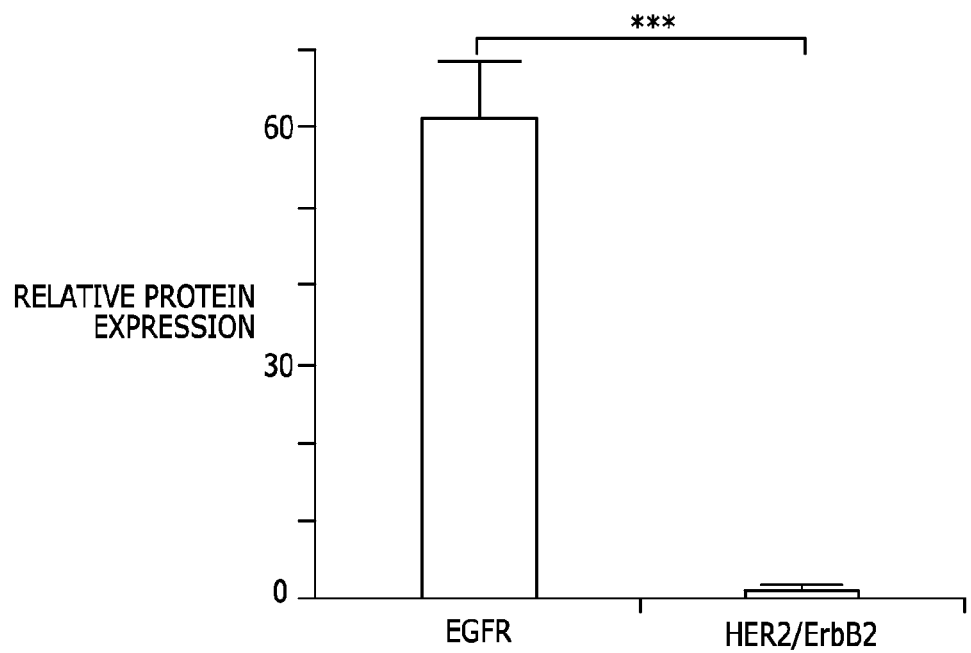

In vivo fluorescence microendoscopy indicated peak fluorescence intensity and tumor selectivity 8-24 hours following Cet-BPD administration (FIG. 7A), in agreement with Cet-BPD tissue extraction (Pearson correlation r=0.82, n=21, P=$5 \times 10^{-6}$; FIGS. 7B and C). To investigate the origins of tumor-selectivity further, the inventors performed fluorescence microendoscopy using two nonspecific, activatable immunoconjugate controls: (i) IgG-BPD(1:7) using polyclonal IgGs isolated from human serum; and, (ii) Tra-BPD(1:5) using trastuzumab, a humanized anti-HER2 mAb. HER2 is a surface molecule from the EGFR family, but it is not expressed at the same level as EGFR by the EOC cells used in this study (FIGS. 7E and F). Both of the nonspecific immunoconjugate controls had altered pharmacokinetics and reduced tumor-to-tissue ratios (FIG. 7D), underscoring the significance of selecting an appropriate target.

Figure 8A:
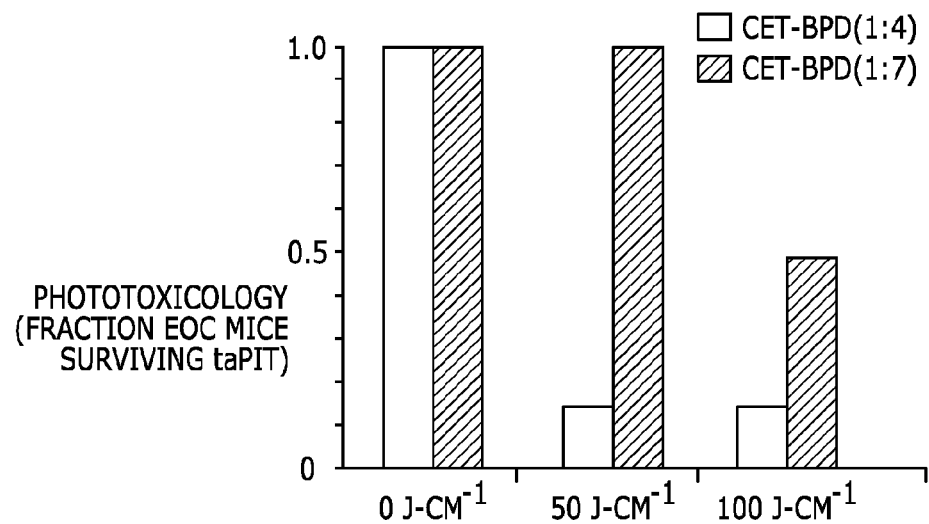
FIG. 8 (A-F) provides graphs and images showing TaPIT toxicology, efficacy and longitudinal monitoring of micrometastatic burden in vivo. (A) Fraction of tumor-bearing mice that survived >72 hours after taPIT. Cet-BPD(1:7) shows increased survival and reduced nonspecific phototoxicity compared to Cet-BPD(1:4). Cet-BPD(1:4): 0 (n=9 mice), 50 (n∥10 mice) and 100 J·cm$^{-1}$ (n=10 mice). Cet-BPD(1:7): 0 (n=16 mice), 50 (n=19 mice) and 100 J·cm$^{-1}$ (n=20 mice). (B) Micrometastatic burden measured by qRT-PCR: no tumor control, n∥4 mice; no treatment, n=30 mice.

TaPIT selectively destroys micrometastases. There is a critical need for tumor-selective therapies that can address residual micrometastases. Above the inventors demonstrated that Cet-BPD(1:7) is activated selectively within tumors, resulting in enhanced tumor fluorescence contrast compared to 'always on' agents. The inventors next tested if this tumor-selective activation translates to a reduction in non-specific phototoxicity. The fraction of EOC mice surviving taPIT, reflecting treatment safety and reduced toxicity in non-target tissues, was enhanced for Cet-BPD(1:7) versus a non-optimal immunoconjugate with lower quenching—Cet-BPD(1:4) (FIG. 8A). Furthermore, bowel histology confirmed that high-dose taPIT with Cet-BPD(1:7) does not cause bowel damage.

The light doses of 50-100 J·cm$^{-1}$ per quadrant and the BPD dose of 2 mg·kg$^{-1}$ enabled by taPIT exceed the maximum tolerated photodynamic dose—the maximum product of the light dose and the photodynamic agent dose at which 100% of EOC mice survive treatment—for non-targeted, 'always on' verteporfin (8 J·cm$^{-1}$ per quadrant at a BPD dose of 0.25 mg·kg$^{-1}$)(Molpus K L et al. Cancer Research 56:1075-1082 (1996)) by an order-of-magnitude (~50-fold). Furthermore, taPIT enables a ~17-fold increase in the maximum tolerated photodynamic dose compared to targeted, 'always on' immunoconjugates for PIT (0.5-1 mg·kg$^{-1}$ photodynamic agent with 3-6 J·cm$^{-1}$ per quadrant). Goff et al., Br J Cancer 74:1194-1198 (1996). Thus, taPIT enables unprecedented photodynamic doses for treating disseminated metastatic disease by overcoming nonspecific toxicities associated with—both targeted and non-targeted—'always on' agents.

Figure 8B:
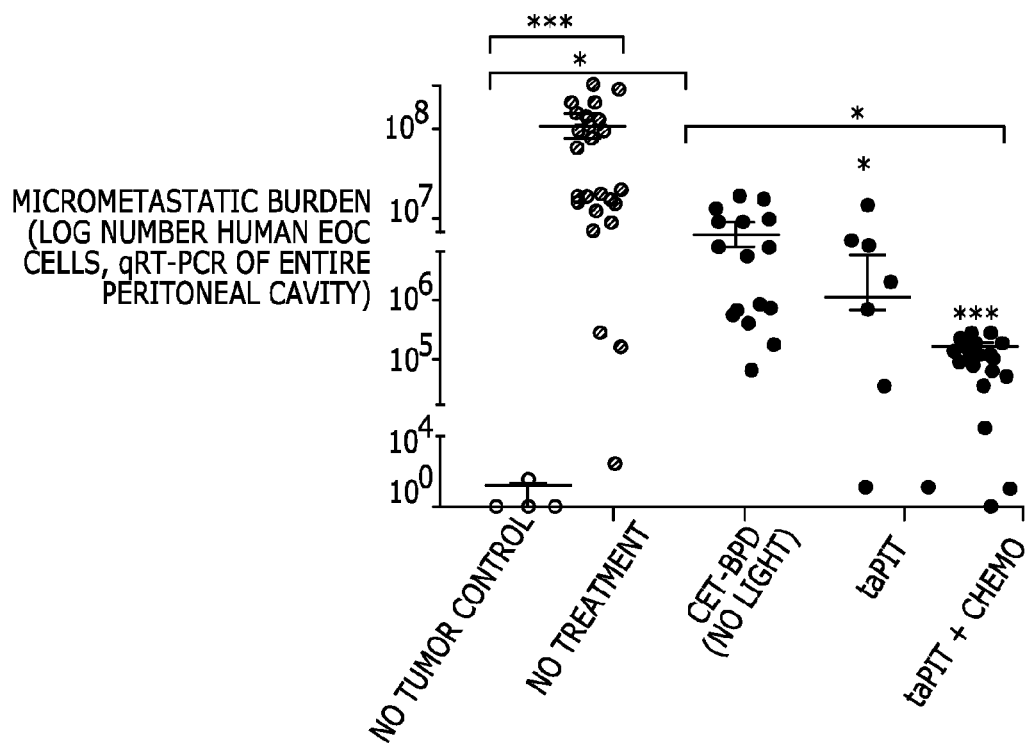

To explore the potency of high-dose taPIT against microscopic tumors in large cavities, EOC mice bearing disseminated micrometastases were treated using a diffusing tip fiber for wide-field irradiation (FIG. 4F). A quantitative reverse transcription polymerase chain reaction (qRT-PCR) assay was employed to assess the number of viable, human EOC cells rigorously in biopsies and entire peritoneal cavities following treatment. Control, untreated EOC mice were characterized for the final tumor burden by qRT-PCR at time points matched to the various treatment courses. Treated mice received intraperitoneal administration of the immunoconjugate in the presence or absence of photoactivation. The inventors observed a trend in reduced number of EOC cells using Cet-BPD(1:7) in the absence of photoactivation (FIG. 8B), which indicates that Cet-BPD possesses similar anti-EGFR and anti-tumor activity to cetuximab monotherapy. del Carmen M G et al., J Natl Cancer Inst 97:1516-1524 (2005). NIR photoactivation for taPIT (2 cycles) achieved a statistically significant mean reduction in tumor burden of 89% relative to untreated mice (FIG. 8B). This level of tumor reduction matches the synergistic reduction found using unconjugated BPD (2 cycles) and cetuximab (4 cycles) in combination. As a benchmark for nearly complete response, taPIT (1 cycle) with follow-up combination platinum- and taxane-based chemotherapy (1 cycle) achieves 97% mean tumor burden reduction (FIG. 8A; a second cycle added no significant benefit). As a further comparative benchmark, prior work indicates 10% and 50% tumor burden reduction for 1 and 2 cycles, respectively, of combination cisplatin plus paclitaxel chemotherapy—at the same doses used here (Materials and Methods)—in this mouse model of metastatic ovarian cancer. Rizvi et al., Isr J Chem 52:776-787 (2012). The relatively poor response to chemotherapy alone may be due to intrinsic resistance—the OVCAR5 cells used in this model have 7-fold resistance to cisplatin relative to a platinum sensitive cell line and contain a subpopulation of stem-like cells that are stimulated by chemotherapy.

Figure 8C:
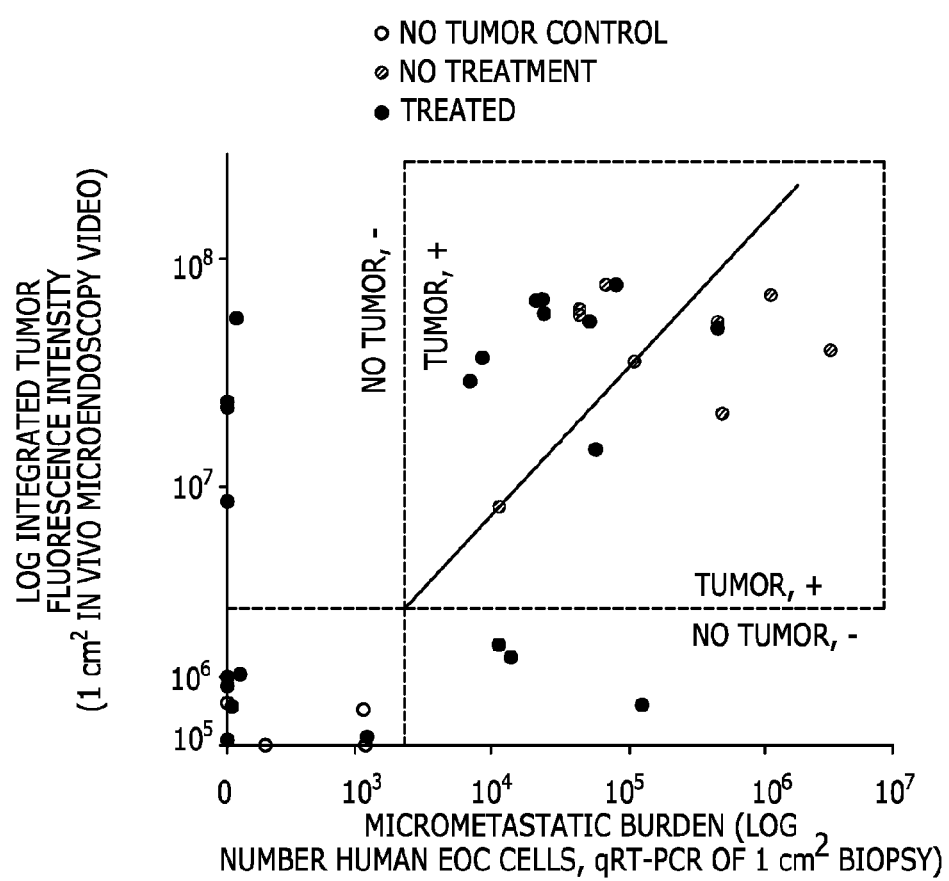

Longitudinal micrometastatic burden monitoring. A key challenge associated with micrometastatic disease is the lack of imaging modalities capable of resolving and monitoring microscopic tumors. Building on the selective accumulation of activated Cet-BPD in micrometastases, which enables accurate recognition of microscopic tumors in untreated mice, the inventors developed micrometastatic burden monitoring using longitudinal fluorescence microendoscopy. The image analysis workflow described above was used as a surrogate marker for micrometastatic burden (FIG. 10). This surrogate was compared with the qRT-PCR assay in matched biopsy specimens from individual untreated and treated EOC mice. Validation of fluorescence microendoscopy tumor monitoring by qRT-PCR indicates a significant Spearman correlation r=0.59 (P=0.0001) and a tumor recognition sensitivity=86% and specificity=73%, n=37 mice (FIG. 8C). The gray regions in FIG. 8C define the true negatives (bottom left; using control no tumor mice to define the bounds) and true positives (upper right). The false positive and negative outliers are treated mice. False positives are due to residual, tumor-associated inflammation. False negatives are likely due to insufficient sampling of the residual disease after treatment. Exclusion of treated mice results in a Spearman correlation r=0.70 (P=0.004) and a tumor recognition sensitivity=100% and specificity=100%, n=15 mice.

Figure 8D:
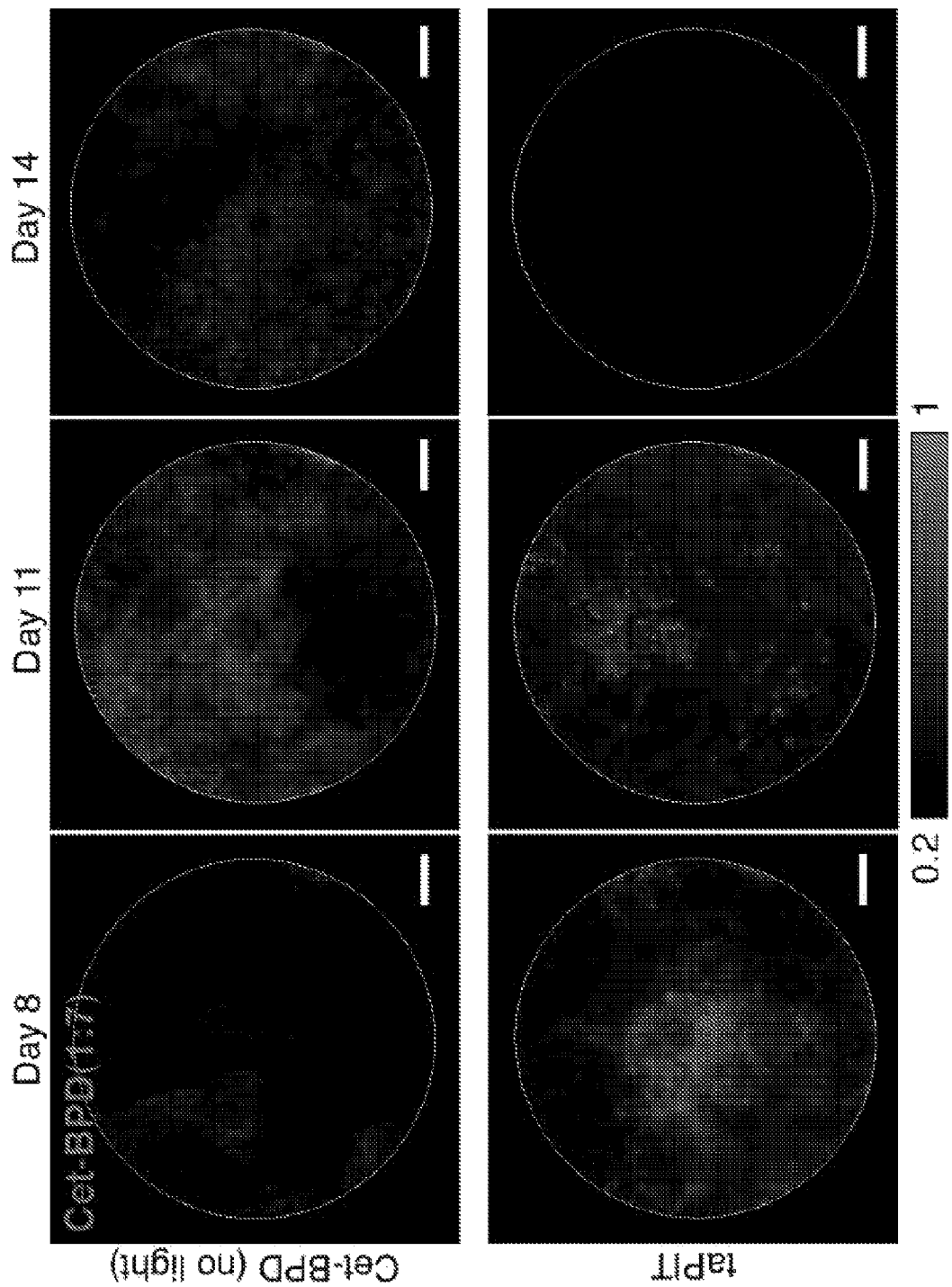
Figure 8E:
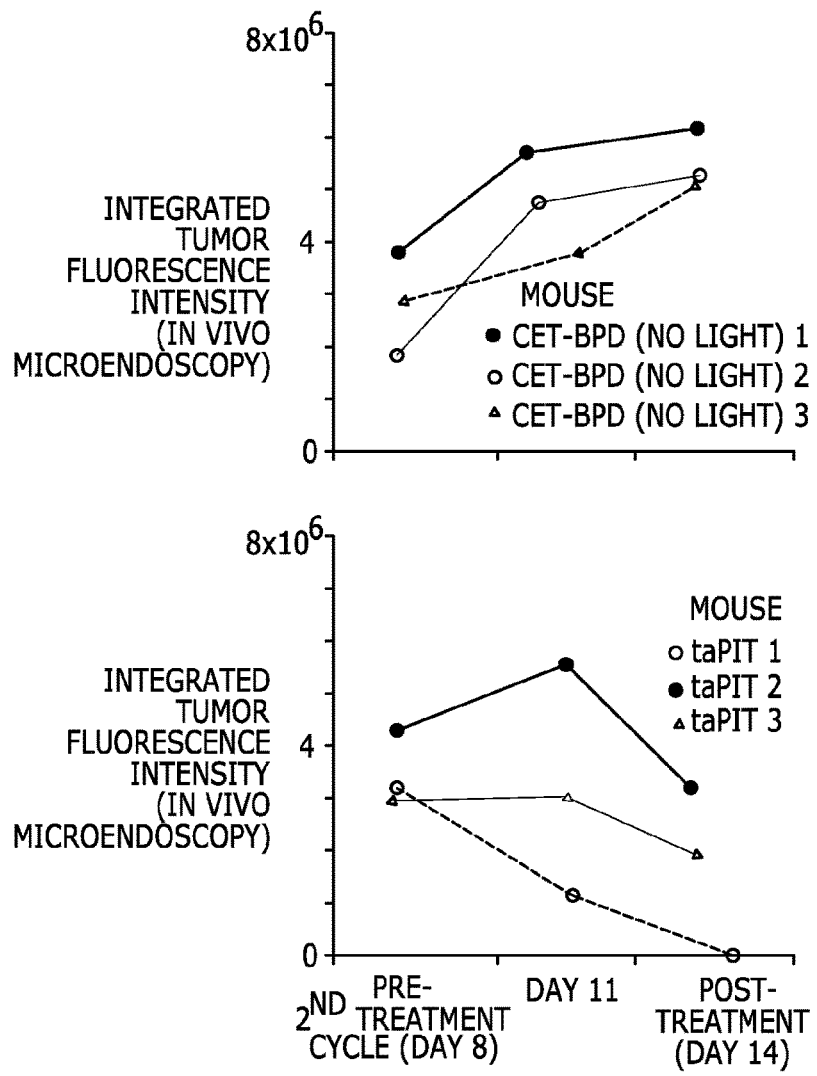
Figure 8F:
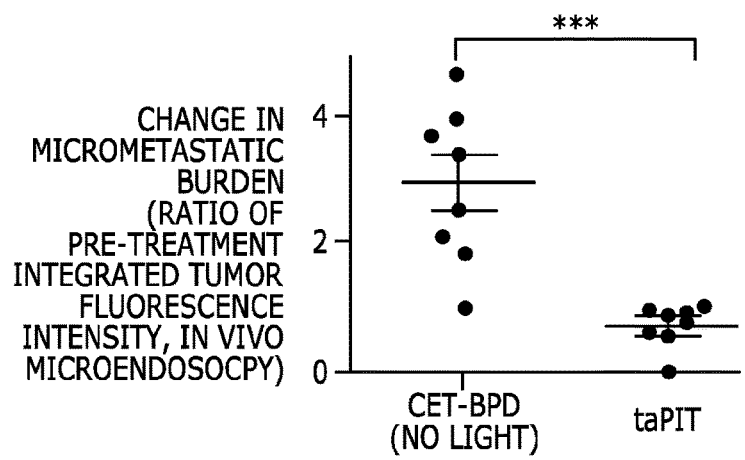

Longitudinal fluorescence microendoscopy imaging of tumor burden in mice receiving taPIT versus Cet-BPD (without photoactivation) is shown over time (FIGS. 8D and E). In each mouse receiving taPIT, the integrated tumor fluorescence decreased markedly between days 11 and 14. Note that taPIT was also performed on day 5, thus, some of these mice display reductions in tumor burden prior to day 8. Using the same metric, mice exposed to Cet-BPD (without photoactivation) showed evidence of increasing tumor burden (FIG. 8D). These data demonstrate that when the pre-treatment tumor burden is taken into account, the enhanced therapeutic efficacy of taPIT over Cet-BPD (without photoactivation) is clearly resolved (FIG. 8F). Without this correction, treatment efficacy is more difficult to discern due to the intrinsic heterogeneity of microscopic disease. Thus, quantitative micrometastatic burden imaging will be critical for evaluation of treatment efficacy in preclinical and clinical studies of residual microscopic disease.

Figure 9A:
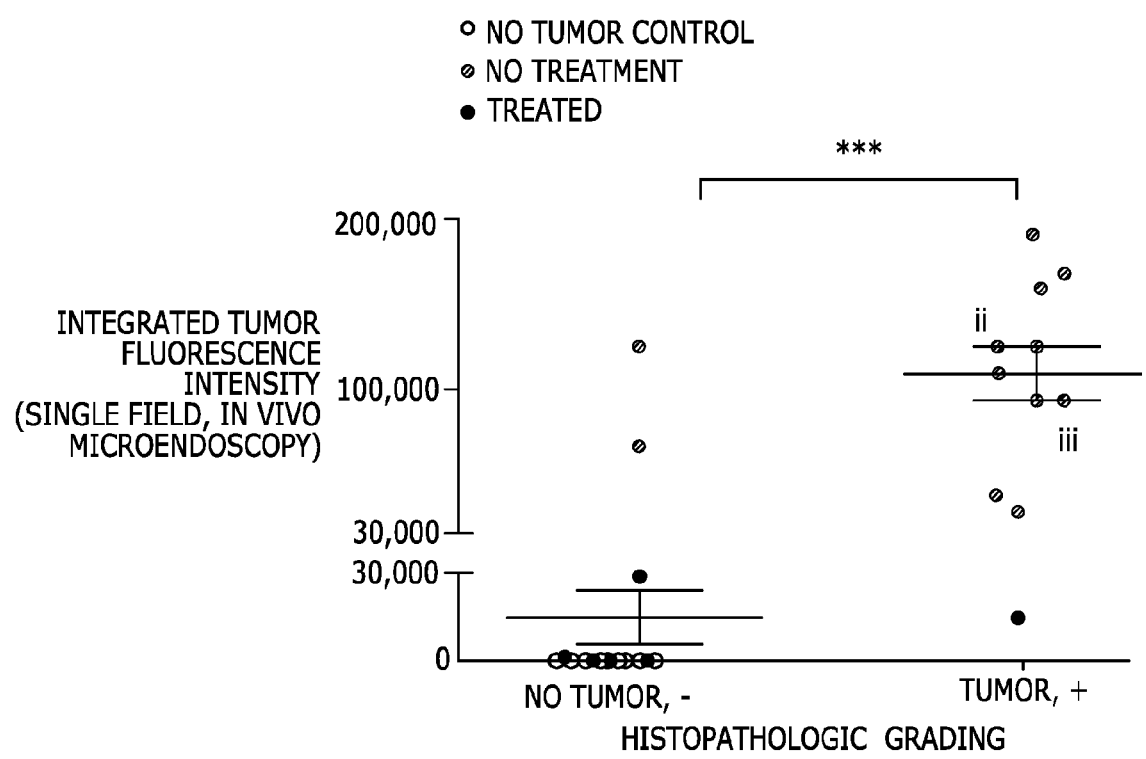
Figure 9B:
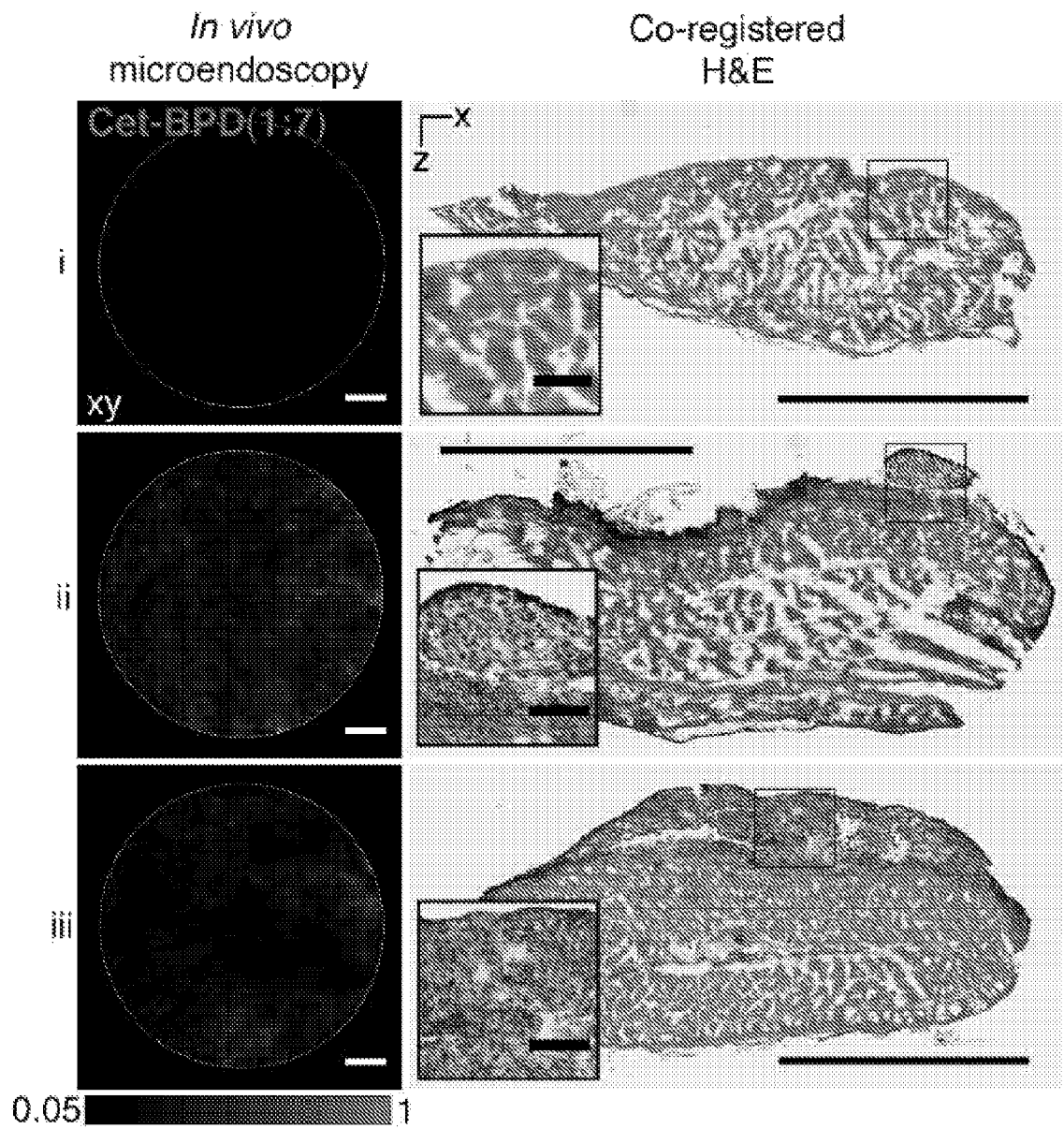

To probe tumor recognition accuracy further, the inventors collected punch biopsies for histopathology co-registered with in vivo fluorescence microendoscopy images. A blinded pathologist graded the hematoxylin and eosin (H&E) stained sections as either 'no tumor, −' in the absence of clear tumor nodules or 'tumor, +' in the presence of multicellular tumor nodules. The resulting histopathologic grades are compared to integrated, in vivo tumor fluorescence (FIG. 9B). The integrated tumor fluorescence was significantly lower for 'no tumor, −' than for 'tumor, +' biopsies (FIG. 9A). In fields where Cet-BPD fluorescence couldn't be detected, no tumor was observed by histopathology. These data provide a further validation of in vivo fluorescence microendoscopy, indicating a tumor recognition sensitivity=91% and specificity=88%, n=13 mice (27 fields). Finally, histopathologic review of these punch biopsies provides further evidence of tumor destruction by taPIT and taPIT with follow-up chemotherapy.

Discussion

Tumor-targeted, activatable PIT is a new therapeutic modality that achieves selective treatment of residual and micrometastatic cancer. Uniquely, Cet-BPD incorporates two synergistic therapies into a single agent—with the photocytotoxic component remaining quenched in nonspecific tissues—to realize a molecular-targeted, activatable therapy. Because cancer cells overexpressing the target surface molecules take up immunoconjugates efficiently (Urano et al., Nat Med 15:104-109 (2008)), this activation occurs predominantly within tumors while unbound conjugates remain quenched. Enhanced lysosomal catabolism of immunoconjugates—which ultimately activates photocytotoxicity and fluorescence—is also expected in cancer cells due to their frequent, high up-regulation of cysteine cathepsin proteases. Mohamed M M, Sloane B F., Nat Rev Cancer 6:764-775 (2006). This tumor-targeted activation enhances contrast for imaging and selective therapy of micrometastases, minimizing background fluorescence and toxicity to vital tissues.

Prior elegant works have demonstrated selective tumor imaging using activatable contrast agents, primarily of macroscopic tumors. Weissleder et al., Nat Biotechnol 17:375-378 (1999); Liu et al., Bioconjug Chem 22:1021-1030 (2011); Lovell J F et al., Nat Mater 10:324-332 (2011). However, these probes have not been used to treat micrometastases, largely due to the fact that fluorescence-guided surgery is impractical at the microscopic scale. In addition, quantitative imaging of microscopic tumor deposits has yet to be investigated using 'always on' or activatable probes. Here the inventors show—importantly, in a disease model that presents challenges to selectivity encountered in the clinic—that directly targeting the cancer cells for immunoconjugate activation enables not only enhanced treatment selectivity but also resolution of individual micrometastases.

PIT is an emerging treatment modality that bolsters the armamentarium of cancer treatments. Photodynamic therapy and PIT induce cytotoxicity using mechanisms that are distinct from traditional therapies to overcome resistance and stimulate, rather than suppress, anti-tumor immunity. For example, photodynamic action can trigger apoptosis through direct photodamage of Bcl-2 protein (Kessel D, Med Laser Appl 21:219-224 (2006)), which is a major cause of radio- and chemoresistance. Reed J C et al., J Cell Biochem 60:23-32 (1996). With the frequent use of fiber optics in medical procedures, light delivery can be and has been successful clinically in complex anatomical sites such as the peritoneal cavity and the lung. Therefore, in the clinic, these agents are photoactivated intraoperatively or endoscopically. Early clinical trials demonstrated feasibility and efficacy for photodynamic therapy of peritoneal metastases with the major challenge being bowel perforations resulting from a lack of tumor selectivity. TaPIT overcomes this poor tumor selectivity and bowel toxicity. In contrast to conventional PIT and photodynamic therapy, the enhanced therapeutic index of taPIT addresses challenges associated with the delivery of treatment to microscopic disease spread throughout large sites such as the peritoneal cavity.

Microendoscopy has taken microscopy to new depths in vivo utilizing miniaturized optics, and this technology is emerging for 'optical biopsy' of cancer. Williams R M., et al. Translational Oncology 3:181-194 (2010); Pierce M C et al., Cancer Prev Res (Phila) 5:1273-1279 (2012). Through the development of in vivo fluorescence microendoscopy with activatable immunoconjugates and automated image analysis algorithms (FIG. 10), the inventors demonstrated that it is possible to monitor micrometastases longitudinally. The sensitivity and specificity of ~90% achieved here for untreated tumors as small as 30 μm represents a significant improvement over the 86% and 53% tumor sensitivity and specificity reported for 'always on' verteporfin. Zhong et al., Br J Cancer 101:2015-2022 (2009). This level of selectivity also results in a two order-of-magnitude improvement in tumor imaging resolution compared to current clinical imaging technologies (e.g., positron emission tomography, computed tomography and magnetic resonance imaging), which have 40-50% sensitivity for subcentimeter tumors. These developments address the lack of imaging technologies for detecting and monitoring micrometastatic disease and open the door to patient-tailored therapeutic regimens based upon real-time feedback regarding the presence and response of residual disease. Here the inventors also developed fluorescence microendoscopy for pharmacokinetic imaging to shape dosimetry decisions and to inform tumor recognition algorithms (FIG. 7 and FIG. 10). The miniature size and mechanical flexibility of fiber-optic fluorescence microendoscopy enable minimally invasive and repeated quantification of micrometastases.

Presently it is only practical to sample some—but not all—of the total micrometastatic burden by microendoscopy due to the microscopic field-of-view, whereas taPIT can be applied for wide-field treatment of large regions of the body harboring disseminated tumors efficiently without the need to first visualize each micrometastasis. Future microendoscope designs may use larger fiber bundles—or foveated lens systems (Hagen N, Tkaczyk T S, J Biomed Opt 17:021104 (2012))—to expand the field-of-view and to enable scanning comparable to conventional laparoscopy.

In the clinic, a number of obstacles have hampered attempts to address cancer micrometastases despite their critical role in treatment failure. Two major barriers are the inability to detect residual tumor deposits until macroscopic recurrence and poor patient tolerance of the chemotherapy dose intensities needed for tumor response coupled with the emergence of chemoresistance. The enhanced tumor selectivity realized by tumor-targeted, activatable immunoconjugates, along with evidence that PIT is effective against drug-resistant cells, offers promise to help overcome these hurdles. TaPIT holds potential to improve cancer survival by leveraging the distinct mechanisms of photodynamic action (Kessel D, Med Laser Appl 21:219-224 (2006)) to treat drug-resistant cells (Celli et al., Lasers Surg Med 43:565-574 (2011)) and reverse chemoresistance (Duska et al., J Natl Cancer Inst 91:1557-1563 (1999)), thereby reducing the number of cycles of chemotherapy needed to elicit tumor destruction (Rizvi et al., Isr J Chem 52:776-787 (2012)). In addition, rationally designed immunoconjugates simultaneously inhibit treatment survival signaling pathways (e.g., the EGFR pathway) in concert with their photocytotoxic effects. Molecular tumor-targeting also provides opportunities for fluorescence-guided surgery to remove more disease prior to taPIT and chemotherapy. Nguyen et al., Proc Natl Acad Sci USA 107:4317-4322 (2010).

Thus, activatable immunoconjugates show promise for clinical translation to address recurrent cancers by facilitating fluorescence-guided resection of macroscopic tumors and fluorescence microendoscopy-guided taPIT to destroy, monitor and potentiate follow-up chemotherapy of residual microscopic disease. In regards to therapy monitoring, the same phenomenon of tumor-targeted activation for PIT also enables detection of residual microscopic disease in critical areas using fluorescence microendoscopy, which may ultimately facilitate the clinical diagnosis of recurrent disease at earlier time points than possible using traditional technologies.

Materials and Methods

Micrometastatic mouse model. An orthotopic xenograft mouse model of human ovarian carcinomatosis was established in our laboratory with gynecologic oncologists (30). Athymic Swiss female Nu/Nu mice (20-25 grams and 6-8 weeks old; Cox Breeding Laboratories) were injected intraperitoneally (i.p.) with $16 \times 10^6$ NIH:OVCAR5 (EOC) cells in 2 mL phosphate-buffered saline. All experiments were conducted according to Massachusetts General Hospital Institutional Animal Care and Use Committee (IACUC) guidelines.

Immunoconjugate synthesis. Conjugates of BPD and mAb (Cet or Tra) or human polyclonal antibody (IgG; 14506, Sigma-Aldrich) were prepared by modifying a previous protocol (Savellano M D, Hasan T, Photochem Photobiol 77:431-439 (2003)) for large-scale synthesis and administered at 2 mg·kg$^{-1}$ body weight BPD, except in FIG. 5B for which an equivalent mAb dose was used (1.4 mg cetuximab) to ensure identical mAb pharmacokinetics for quantitative assessment of nonspecific fluorescence. Briefly, the N-hydroxysuccinimide ester of BPD was reacted with antibody, which had previously been polyethylene glycolated. The resulting immunoconjugate was purified using a Zeba spin desalting column (Thermo Scientific). The purity of the immunoconjugates is high—as assessed by gel fluorescence imaging analysis following sodium dodecyl sulfate polyacrylamide gel electrophoresis—with less than 5% residual unconjugated BPD impurity (an upper bound since fluorescence quenching of conjugated BPD was not taken into account). The molar ratio of BPD to antibody was measured using a BCA protein assay (Pierce) and BPD absorbance spectroscopy at 690 nm.

Intraperitoneal taPIT and chemotherapy. EOC mice were randomized into the following groups: (i) no treatment; (ii) Cet-BPD without taPIT (0 J·cm$^{-1}$), 1 cycle; (iii) Cet-BPD without taPIT (0 J·cm$^{-1}$), 2 cycles; (iv) Cet-BPD with taPIT (50 J·cm$^{-1}$), 2 cycles; and, (v) Cet-BPD with taPIT (50-100 J·cm$^{-1}$), combined with 3-5 and 10-15 mg·kg$^{-1}$ body weight of cisplatin and paclitaxel, 1-2 cycles. All injections were done i.p. in 1 mL of sterile phosphate-buffered saline. The BPD dose was fixed at 2 mg·kg$^{-1}$ body weight. For Cet-BPD(1:7), the cetuximab dose was 1.4 mg, which is equivalent to ~180 mg·m$^{-2}$ and near the clinical cetuximab dose of 250-400 mg·m$^{-2}$. Treatment-associated mortality is defined as mice surviving less than 72 hours after treatment. Mice were illuminated 8-24 hours (taPIT) after immunoconjugate injection as follows. Mice were anesthetized with isoflurane during treatment and imaging. The light doses are defined as the energy delivered per unit length of the diffusing fiber tip per peritoneal quadrant (i.e., one-fourth of the total fluence per mouse). The inventors performed i.p. light irradiation as previously described. del Carmen et al., J Natl Cancer Inst 97:1516-1524 (2005). Briefly, all mice were injected i.p. with 2 mL of a 0.1% intralipid solution (Baxter Healthcare) to enhance light scattering. A cylindrically diffusing-tip fiber, connected to a 690 nm diode laser (High Power Devices), was introduced into the peritoneal cavity of a supine anesthetized animal via a centrally placed 14-gauge catheter that traversed the peritoneal wall. The 690 nm light was delivered at an irradiance of 150 (for 50 J·cm$^{-1}$ taPIT) or 300 mW·cm$^{-1}$ (for 100 J·cm$^{-1}$ taPIT). One-fourth of the total light energy was delivered to each intraperitoneal quadrant over equivalent periods.

Fluorescence microendoscope. The custom-built microendoscope uses a blue light-emitting diode (LXHL-LR5C, Luxeon Star LEDs) excitation source, a 10× objective (NT46-144, Edmund Optics) and a dichroic mirror (500dcxr, Chroma Technology). Zhong W et al., Br J Cancer 101:2015-2022 (2009). The beam was focused onto the proximal end and transmitted to the distal end of a 1.5 m-long, 800-μm-diameter and 0.35 NA flexible coherent fiber bundle (IGN-08/30, Sumitomo Electric USA), delivering an optical power of 0.25 mW during contact mode imaging of the sample. The coherent fiber bundle consists of 30,000 cores. The core-to-core spacing is ~4.4 w, sufficient for cellular resolution imaging. Fluorescence emission was collected by the fiber probe through an emission filter (D700/40, Chroma Technology) onto an electron-multiplying CCD camera (Cascade 512B EMCCD, Photometrics), which has a quantum efficiency of ~90% at the spectral region of the BPD fluorescence emission peak (690-700 nm). The EM gain and exposure time were fixed at 3000 volts and 100 milliseconds throughout the experiments. Analysis of USAF test target images determined 1.6 μm x-y sampling.

In vivo fluorescence microendoscopy. During fluorescence microendoscopy of anesthetized mice (using isoflurane inhalant anesthesia), the inventors acquired 40 snapshots per mouse per time point during 10 frames per second (fps) video preview. The snapshots were distributed evenly amongst the peritoneal wall and pelvic omentum. For fluorescence microendoscopy validation, the inventors marked a 1 cm$^2$ region on the outer peritoneal wall using a tissue marking dye (Mark-It, Richard-Allan Scientific), after peeling back the neighboring skin. The inventors then collected a 10 fps in vivo fluorescence microendoscopy video of Cet-BPD(1:7) fluorescence by scanning over the inner peritoneal wall within the marked region. To perform fluorescence microendoscopy-guided biopsy, the inventors then placed the microendoscope tip at a field of interest and marked the location with a dot of marking dye on the outer wall. The square piece of tissue was then excised and the inventors collected the marked location using a punch biopsy (3-mm-diameter, Miltex), followed by immediate embedding and freezing of the biopsy in optimal cutting temperature compound for frozen sectioning on a microtome-cryostat. The inventors avoided directly handling tissue biopsies by dispensing them onto lens paper followed by application of embedding medium. The tissue paper was then held vertically in cryomolds using forceps to orient the punch biopsies for vertical sectioning, perpendicular to the peritoneal wall surface. This procedure enables co-registered microendoscope images and biopsy specimens for histopathology and immunofluorescence staining. The square piece of tissue was then snap frozen for qRT-PCR to compare to tumor burden assessment by fluorescence microendoscopy. Verteporfin and Cet-BPD were administered at equivalent BPD doses (2 mg·kg$^{-1}$ body weight), except for (FIG. 5B) as noted above.

Fluorescence microendoscopy image analysis. For the control no tumor mice the inventors calculated the mean fluorescence signal intensity and calculated an intensity threshold set to classify 99.5% of the pixels as 'no tumor' (FIG. 11). For the EOC mice the inventors calculated the mean fluorescence signal intensity for pixels above the 'no tumor' threshold, and only for objects greater than 30 μm in dimension based on the ROC analysis (FIG. 6). The reported values for EOC mice were calculated from the five brightest images per mouse. In all cases the mean autofluorescence intensity (determined by imaging mice prior to immunoconjugate injection) was subtracted, and an automated routine was used to select the fiber bundle in each image for analysis (indicated by a white circle in the figures). All analyses were performed using a custom Matlab routine for batch image processing (FIG. 10).

Statistical analysis. Statistical analyses were carried out using GraphPad Prism (GraphPad Software). Specific statistical tests are indicated in the figure captions. Tumor burden reduction data amongst multiple treatment groups were analyzed using a Kruskal-Wallis one-way ANOVA following a Grubbs' test that identified statistical outliers. No more than one outlier was removed per treatment group. Two-tailed P-values are reported for Pearson and Spearman correlation coefficients. The Spearman correlation coefficients (representing nonlinear, monotonic correlations) were used for micrometastatic burden imaging validations since integrated tumor fluorescence scales as a power law with tumor volume.

Additional details on experimental procedures and data processing used for this study can be found in the SI Text: Fluorescence microendoscope; In vitro validations of Cet-BPD specificity and immunofluorescence stains; Hyperspectral imaging of the peritoneal cavity; BPD quantification by tissue extraction; Pharmacokinetic model; Confocal imaging of freshly excised tissues; Western blots; and, Quantitative RT-PCR measurement of micrometastatic burden.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for evaluating micrometastases in vivo in a tissue region of a subject comprising:
   (a) administering to the subject a detectably effective amount of a tumor-targeted photoactivatable immunoconjugate, wherein the tumor-targeted photoactivatable immunoconjugate is a tumor-targeted antibody linked to a benzoporphyrin derivative that is configured to be dequenched upon intracellular localization into micrometastases in the tissue region;
   (b) allowing a sufficient amount of time for the tumor-targeted photoactivatable immunoconjugate to enter the micrometastases in the tissue region, wherein the micrometastases have a size of 1 mm or less;
   (c) illuminating the tumor-targeted photoactivatable immunoconjugate in vivo;
   (d) obtaining an in vivo image of the tissue region of the subject using a fluorescent imaging device, and
   (e) evaluating the micrometastases in the tissue region by conducting algorithmic analysis of the in vivo image; wherein the algorithmic analysis comprises selecting each pixel within the in vivo image having an intensity value greater than a first threshold value, wherein the first threshold value is calculated from a plurality of intensity values taken from a control environment free of metastases taken at one or more times following single or multiple administrations of the tumor-targeted photoactivatable immunoconjugate and an internal organ tissue-specific pharmacokinetic model, wherein the internal organ tissue-specific pharmacokinetic model is derived using intensity values obtained from background calibration images of corresponding internal organ tissue;
      clustering the selected pixels to form at least one object;
      rejecting any object having a largest dimension less than a second threshold value; and
      calculating an aggregate intensity value for each object as the sum of the intensity values of the selected pixels comprising the object where each pixel intensity value is corrected using a tissue-specific pharmacokinetic model database.

2. The method of claim 1, wherein the intensity value for each pixel comprises a ratio of a raw intensity value of the pixel to a calibration value representing an intensity of the photoactivatable immunoconjugate.

3. The method of claim 1, the method further comprising determining an average background intensity value for a given type of internal organ tissue associated with the tissue region, the intensity value for each pixel comprising a ratio of a difference between a raw intensity value of the pixel and a background intensity of the photoactivatable immunoconjugate and a background intensity value.

4. The method of claim 1, further comprising applying a mask to the in vivo image, such that pixels that are not expected to be illuminated by the fluorescent imaging device are excluded from the analysis;
   calculating an autofluorescence intensity value as an average intensity value for all pixels not excluded by the mask; and
   subtracting the autofluorescence intensity value from the intensity value for each pixel.

5. The method of claim 1, further comprising applying a Gaussian noise filter to the in vivo image.

6. The method of claim 1, wherein the benzoporphyrin derivative is verteporfin.

7. The method of claim 1, further comprising using a microendoscope to obtain the in vivo image.

8. A method for in vivo treatment of micrometastases in a tissue region of a subject, comprising:
   (a) administering to the subject a therapeutically effective amount of a tumor-targeted photoactivatable immunoconjugate, wherein the tumor-targeted photoactivatable immunoconjugate is a tumor-targeted antibody linked to a benzoporphyrin derivative that is configured to be dequenched upon intracellular localization into micrometastases in the tissue region;
   (b) allowing a sufficient amount of time for the tumor-targeted photoactivatable immunoconjugate to enter the micrometastases in the tissue region, wherein the micrometastases have a size of 1 mm or less;
   (c) photoactivating the tumor-targeted photoactivatable immunoconjugate in vivo to treat the micrometastases;
   (d) obtaining an in vivo image of the tissue region of the subject using a fluorescent imaging device;
   (e) conducting an algorithmic analysis of the in vivo image of the tissue region, wherein the algorithmic analysis comprises selecting each pixel within the in vivo image having an intensity value greater than a threshold value, wherein the first threshold value is calculated from a plurality of intensity values taken from a control environment free of metastases taken at one or more times following single or multiple administrations of the tumor-targeted photoactivatable immunoconjugate and an internal organ tissue-specific pharmacokinetic model, wherein the internal organ tissue-specific pharmacokinetic model is derived using intensity values obtained from background calibration images of corresponding internal organ tissue;
      clustering the selected pixels to form at least one object;
      rejecting any object having a largest dimension less than a second threshold value; and
      calculating an aggregate intensity value for each object as the sum of the intensity values of the selected pixels comprising the object where each pixel intensity value is corrected using a tissue-specific pharmacokinetic model database, and
   (f) providing additional treatment if imaging of the tissue region indicates that a significant number of micrometastases remain in the tissue region, wherein the additional treatment is selected from administering additional tumor-targeted photoactivatable immunoconjugate, cryoablation, thermal ablation, radiotherapy, radiofrequency ablation, electroporation, alcohol ablation, high intensity focused ultrasound, or administration of an anticancer agent.

9. The method of claim 8, wherein the tumor-targeted photoactivatable immunoconjugate is epidermal growth factor receptor specific.

10. The method of claim 8, wherein the tumor-targeted photoactivatable immunoconjugate comprises a plurality of quenched photoactivatable compounds.

11. The method of claim 8, wherein the benzoporphyrin derivative is verteporfin and the micrometastases comprise ovarian cancer cells.

12. The method of claim 8, further comprising using a microendoscope to obtain the in vivo image.

13. The method of claim 8, wherein the intensity value for each pixel comprises a ratio of a raw intensity value of the pixel to a calibration value representing an intensity of the photoactivatable immunoconjugate.

14. The method of claim 8, the method further comprising determining an average background intensity value for a given type of internal organ tissue associated with the tissue region, the intensity value for each pixel comprising a ratio of a difference between a raw intensity value of the pixel and a background intensity value to a difference between a calibration value representing an intensity of the photoactivatable immunoconjugate and the background intensity value.

15. The method of claim 8, further comprising:
applying a mask to the in vivo image, such that the pixels that are not expected to be illuminated by the fluorescent imaging device are excluded from the analysis;
calculating an autofluorescence intensity value as an average intensity value for all pixels not excluded by the mask; and
subtracting the autofluorescence intensity value from the intensity value for each pixel.

16. The method of claim 8, further comprising applying a Gaussian noise filter to the in vivo image.

\* \* \* \* \*

UNITED STATES PATENT AND TRADEMARK OFFICE
CERTIFICATE OF CORRECTION

| | |
|---|---|
| PATENT NO. | : 11,547,300 B2 |
| APPLICATION NO. | : 15/114881 |
| DATED | : January 10, 2023 |
| INVENTOR(S) | : Tayyaba Hasan et al. |

It is certified that error appears in the above-identified patent and that said Letters Patent is hereby corrected as shown below:

In the Specification

Column 31, Line 64, "~4.4 w" should be --~4.4 µm--.

In the Claims

Claim 8, Column 34, Line 53, "of corresponding" should be --of the corresponding--.

Signed and Sealed this
Sixteenth Day of May, 2023

Katherine Kelly Vidal
*Director of the United States Patent and Trademark Office*